US010518079B2

(12) United States Patent
Li

(10) Patent No.: US 10,518,079 B2
(45) Date of Patent: Dec. 31, 2019

(54) SYSTEM AND METHODS TO MODULATE AN ELECTRIC FIELD IN AN ENVIRONMENT

(71) Applicant: Zhen Li, Toronto (CA)

(72) Inventor: Zhen Li, Toronto (CA)

(*) Notice: Subject to any disclaimer, the term of this patent is extended or adjusted under 35 U.S.C. 154(b) by 0 days.

(21) Appl. No.: 16/503,573

(22) Filed: Jul. 4, 2019

(65) Prior Publication Data

US 2019/0329021 A1    Oct. 31, 2019

Related U.S. Application Data

(63) Continuation-in-part of application No. 15/784,073, filed on Oct. 13, 2017.

(30) Foreign Application Priority Data

Oct. 14, 2016   (CA) ..................... 2945343

(51) Int. Cl.
| | |
|---|---|
| *A61N 1/20* | (2006.01) |
| *A61N 1/02* | (2006.01) |
| *A61N 1/04* | (2006.01) |
| *H02M 3/155* | (2006.01) |
| *H02M 7/06* | (2006.01) |

(52) U.S. Cl.
CPC ......... *A61N 1/0408* (2013.01); *A61N 1/0404* (2013.01); *H02M 3/155* (2013.01); *H02M 7/06* (2013.01)

(58) Field of Classification Search
CPC .......... A61N 1/205; A61N 1/10; A61N 1/025; A61N 1/0404; A61N 1/0408; A61H 39/08
See application file for complete search history.

(56) References Cited

U.S. PATENT DOCUMENTS

| | | | | |
|---|---|---|---|---|
| 849,653 | A * | 4/1907 | Bachelet | A61N 2/02 600/13 |
| 3,311,108 | A * | 3/1967 | Cristofv | A61N 1/10 128/202.25 |
| 3,678,337 | A * | 7/1972 | Grauvogel | A61N 1/10 361/231 |

(Continued)

FOREIGN PATENT DOCUMENTS

| | | | |
|---|---|---|---|
| CA | 1075319 A1 * | 4/1980 | |
| FR | 976815 * | 3/1951 | |

*Primary Examiner* — Matthew F Desanto

(57) ABSTRACT

A system and methods are provided for simulating a fair weather electric field in an environment to promote the well-being of a subject. A converter provides a DC output to generate a DC electric field in between positive and negative electrodes in an environment, where the positive electrode is proximal to a positive part of a subject and the negative electrode is proximal to a negative part of the subject. An electric field detector measures and transmits data about the strength of the actual electric field in the environment. A microprocessor receives the data and compares the information to the parameters of a fair weather electric field to direct the function of a pulse width modulator, modulate the DC output and thereby simulate the fair weather electric field in real-time. Means are provided for filtering out over-voltages, pulses and over-currents to ensure the controlled modulation of the DC electric field.

16 Claims, 23 Drawing Sheets

(56) References Cited

U.S. PATENT DOCUMENTS

| | | | | | |
|---|---|---|---|---|---|
| 3,781,636 | A | * | 12/1973 | Genuit | H02M 3/3155 |
| | | | | | 361/90 |
| 4,094,322 | A | * | 6/1978 | Hara | A61N 1/40 |
| | | | | | 128/908 |
| 4,517,621 | A | * | 5/1985 | Brusis | A61N 1/10 |
| | | | | | 361/231 |
| 4,802,470 | A | * | 2/1989 | Hara | A61N 1/10 |
| | | | | | 601/15 |
| 6,505,079 | B1 | * | 1/2003 | Foster | A61N 1/08 |
| | | | | | 607/63 |
| 2005/0264427 | A1 | * | 12/2005 | Zeng | H02H 5/12 |
| | | | | | 340/635 |
| 2009/0228084 | A1 | * | 9/2009 | Chen | A61H 39/002 |
| | | | | | 607/115 |
| 2011/0160811 | A1 | * | 6/2011 | Walker | A61H 39/002 |
| | | | | | 607/72 |
| 2012/0143285 | A1 | * | 6/2012 | Wang | A61B 5/024 |
| | | | | | 607/59 |
| 2015/0025421 | A1 | * | 1/2015 | Wagner | A61N 1/36025 |
| | | | | | 601/2 |

* cited by examiner

X-axis present time, one grid presents 18.25 days, the whole scope presents one year. Y-axis present voltage, one grid is 5 V.

X-axis present time, one grid presents 2.4 hours, the whole scope presents 2 days. Y-axis present voltage, one grid is 5 V.

X-axis present time, one grid is 50mS real time presents 18.25 days, the whole scope presents one year; Y-axis present voltage, one grid is 5 V, the curve moves between -22.19 to 22.78 V.

The results of harmonic analysis of fair weather atmospheric field at YBJ, Tibet.

| | Annual | Diurnal | Semi-diurnal | 3rd harmonic | 4th harmonic |
|---|---|---|---|---|---|
| Amplitude/ (V/m) | 24.8 ± 4.5 | 9.7 ± 0.7 | 6.6 ± 0.4 | 4.0 ± 0.4 | 3.3 ± 0.2 |
| Phase | October | 06:30 UT | 05:00 UT | 03:00 UT | 02:30 UT |
| Period | 365 days | 24 h | 12 h | 8 h | 6 h |

Figure 21
Prior Art

SYSTEM AND METHODS TO MODULATE AN ELECTRIC FIELD IN AN ENVIRONMENT

FIELD OF THE INVENTION

The present invention relates to the field of generating, including modulating and simulating wellness promoting electric fields in an environment, and more particularly the generation of smooth, incrementally changing, positive DC electric fields in the vicinity of a subject.

BACKGROUND OF THE INVENTION

The background to the invention provides information about the state of the art relating to the generation of electric fields in the vicinity of subject to simulate environmental conditions which promote wellness and healing.

Modern technologies may bring us a better life in one sense, but at the same time they contaminate or distort the natural conditions of our living environment. These contaminations or disruptions not only include air, water or soil pollution, but also include electric field pollution, and electromagnetic radiation. When natural electric fields are disrupted, or access to them is blocked, the ability of living beings to maintain good health and overall wellness is affected. Examples of technologies which impact natural electric fields are: large generators, which can create unnaturally strong electric fields, and electric power cables, which generate strong AC fields. Modern building and large structures, on the other hand, shield us from the charging effect of the ionosphere, such as the concrete and metal roofing of buildings.

More recently, the multitude of man-made fibers being used in clothing with electrostatic properties create or build unwanted electric fields, such as negative electric fields, fields that change too rapidly, or that are too strong around the subject wearing such clothing.

The impact of these modern living conditions is akin to living under chronic overcast and inclement weather conditions. FIG. 10 provides a schematic representation of how modern living conditions can disrupt, disturb or distort the electric fields around a subject.

The ability to shield ourselves from these contaminations or disturbances and to create a clean and quiet atmospheric-type electric field in our environments can promote recovery from diseases, and general good health. Under fair weather conditions, living creatures or beings (subjects) have a better (healthier) metabolism. On the other hand, bad weather, like storms, rain, overcast skies, especially thunder-storms, causes the nervous system of beings to be unpleasantly affected, and brings on, incites, or aggravates neuralgic, rheumatic and other pains, as well as mental and emotional distress, because there are irregular disturbances in the electrical condition of the atmosphere.

Systems developed previously to create or try to simulate wellness promoting electric fields in an environment have their limitations due to the available technology at the time of their development and insufficient attention or considerations of the characteristics and rhythms of natural electrical fields and how to ensure a subject can experience the full benefits of exposure to wellness promoting electric fields. As a result, many of the known technologies apply an AC (alternating current) electric field, or a very high voltage DC (direct current) electric field (e.g. CN1309889A), which can negatively impact subjects. In CN1309889A high voltage equipment is used to produce a spatial electric field inside a greenhouse between plants and the earth, in order to promote the homogenous absorption of fertilizers and increased plant yields. In other instances technologies have been developed which create negative DC fields not suitable for promoting wellness in a subject.

In still other cases, technologies have been developed that do not provide for adequate electric field modulation or natural electric field simulation. See, for example, CA1075319 which discloses the application of a DC electric field with a short cycle impulse. A constant electric field is created with pulses in the frequency range between approximately 0.1 and 20 Hz, which can have a disruptive effect on living subjects.

Another example of technology which does not provide adequate electric field modulation or natural electric field simulation is FR976815. As disclosed, the system of this patent sets a voltage to create a constant electric field output. No mechanism is provided to modulate in real time the electric field output according to how the field may need to fluctuate to simulate a fair weather electric field, or Carnegie Curve pattern, or to otherwise be adapted (modulated) based on how the actual electric field is being impacted or affected in an environment in the vicinity of a subject. Without real-time modulation, the net (effective) electric field in the environment may in fact end up being very far off from the target strength set using the system disclosed. This is because the actual field changes in unknown ways (i.e. either being augmented or reduced in the vicinity of a subject) due to overlap between the electric field output and other electric fields generated by other sources. There are many electric or electronic products around us that create electric fields. The field overlap might not allow the desired effective strength to be realized based on a single set of settings, or occasional manual manipulation of settings applied when using a system according to the prior art. This can mean not having the positive impact on a subject's wellbeing, or worse, even result in harm to a subject.

There are other systems that have also been developed to either create electric fields in a space, or apply such fields to parts of a subject. Their design, however, results in the creation of fields with uneven or non-uniform strengths in the target environment, relatively large field strength shifts, or sudden field fluctuations in the electric field strength. More specifically, such systems either intentionally apply pulses, or otherwise fail to properly simulate the natural rhythms of fair weather electric field conditions, which result in smooth (slow) and incrementally changing field strengths that have a beneficial effect on the well-being of life forms in an environment.

Accordingly, there remains a need to provide for the controlled and customized modulation of electric fields in our living and healing environments to simulate in the vicinity of a subject naturally occurring electric fields which promote wellness.

SUMMARY OF THE INVENTION

The present invention relates generally to the generation of (including simulation and modulation) of wellness promoting electric fields in the environment of a subject. Systems and methods of generating smooth and incrementally changing (variable), positive electric fields are achieved by a DC electric field generating subsystem whose output is regulated using pulse width modulation, which in turn is controlled and mediated by a microprocessor. The microprocessor is configured to direct the generation of wellness promoting electric fields based on the real-time monitoring of actual electric field conditions (by an electric field detector) in the target environment and processing of said data with reference to parameters for generating desirable electric fields (e.g. simulated fair weather electric fields).

It is an object of the invention to provide a system and methods for generating a no pulse, non-constant, positive (DC) electric field in an environment, which has a good rhythm (e.g. simulates natural, fair weather electrical fields), or in which the positive and negative electrodes of the system associate with the right part of a subject. Such system configurations and electric fields promote wellness, and therefore bring benefit to the subject in the environment where the field is generated and so modulated.

According to one aspect there is provided a method comprising the steps of:
a) providing a DC input to a converter to produce a DC output and generate a DC electric field in a space between a positive electrode and a negative electrode positioned in an environment and operatively associated with the converter;
b) detecting an actual electric field in the space between the positive electrode and negative electrode using a first detector and transmitting information about the actual electric field from the first detector to a microprocessor;
c) processing the information regarding the actual electric field using the microprocessor, the microprocessor being configured to receive and process the information to direct the generation of the DC electric field in real-time such that it simulates a fair weather electric field cycle in the environment; and
d) modulating the strength of the DC electric field using a pulse width modulator operatively associated with a switch to regulate the DC output,
wherein said pulse width modulator and switch are controlled by the microprocessor, which directs the operation of the pulse width modulator and switch to generate the variable electric field.

According to another aspect there is provided a system comprising:
a) a converter for receiving a DC input and producing a DC output to generate a DC electric field in a space between a positive electrode and a negative electrode positioned in an environment and operatively associated with the converter;
b) a first detector for detecting an actual electric field in the space between the positive electrode and negative electrode and transmitting information about the actual electric field;
c) a microprocessor for receiving and processing the information from the first detector about the actual electric field, the microprocessor being configured to process the information to direct the generation of the DC electric field in real-time such that it simulates a fair weather electric field in the environment; and
d) a pulse width modulator operatively associated with a switch to regulate the DC output, said pulse width modulator and switch being controlled by the microprocessor,
wherein the microprocessor directs the operation of the pulse width modulator and switch to modulate the strength of the DC electric field and thereby generate the simulated fair weather electric field.

In certain embodiments of the system and method the DC electric field is a slow fluctuating, no pulse, positive electric field.

In other embodiments of the system and method, a second detector detects an over-voltage and transmits information regarding the over-voltage to the microprocessor to facilitate the adjustment of the DC output.

In still other embodiments of the system and method, a third detector detects an over-current and transmit information about the over-current to the microprocessor to facilitate the adjustment of the DC output.

In yet other embodiments of the system and method, the environment is an enclose space, such as a room, booth, cabin, or bubble enclosure. In related embodiments, the environment is near the surface of a wall, ceiling, floor of the enclosed space.

In further embodiments of the system and method, the environment is around or proximal to an article of furniture, such as a chair, stool, bench, sofa, bed, desk, or table.

In still further embodiments of the system and method, the environment is around or proximal to an article of clothing, such as a shirt, shoe, jacket, coat, hat, dress, skirt, or pants.

In certain embodiments of the system and method, the environment is around or proximal to a transport means, such as a car, truck, bicycle, carriage, cart, scooter, train, plane, snowmobile, skies, skates, or boat.

In some embodiments of the system and method, a subject is in the environment. In related embodiments, the subject is a human. In still other related embodiments, the human subject is practicing Tai Chi or Qigong in the environment. In further embodiments, the human subject is receiving a therapy in the environment, such as acupuncture.

In other embodiments of the system and method, the positive electrode and negative electrode are positioned in the environment in a manner so as be proximal to a positive and negative part, respectively, of the subject. In related embodiments, the positive electrode is proximal to the head of the subject and the negative electrode is proximal to the feet of the subject. In further related embodiments, the positive electrode is proximal to the torso of the subject and the negative electrode is proximal to the feet of the subject.

In still other embodiments of the system and method, the strength of the electric field is greater than 103 V/m and less than 300 V/m at any given point in time.

In yet further embodiments of the system and method, the electric field simulates a Carnegie curve, solar diurnal, annual, monthly, seasonal, fifteen minute, 10 year, 12 year, 60 year, or 180 year wellness promoting electric field cycle.

In yet another aspect there is provided a method comprising the steps of:
a) providing a power source and generating a DC input to a converter to produce a DC output and generate a DC electric field in a space between a positive electrode and a negative electrode where a subject is located, wherein the positive electrode is positioned proximal to the head or torso of the subject and the negative electrode is positioned proximal to the feet or abdomen of the subject;
b) detecting an actual electric field in the space between the positive electrode and negative electrode using a first detector and transmitting information about the actual electric field from the first detector to a microprocessor;
c) processing the information regarding the actual electric field using the microprocessor, the microprocessor being configured to receive and process the information to direct the generation of the DC electric field in real-time such that it simulates a fair weather electric field;
d) modulating the strength of the DC electric field using a pulse width modulator operatively associated with a switch to regulate the DC output, wherein said pulse width modulator and switch are controlled by the microprocessor, which directs the operation of the pulse width modulator and switch to generate the DC electric field that simulates the fair weather electric field;

e) further modulating the DC output by detecting an over-voltage of a voltage as the converter produces the DC output using a second detector and transmitting information regarding the over-voltage to the microprocessor to facilitate the adjustment of the DC output by one or more of the steps of changing a pulse width of a pulse width modulator, storing the over-voltage in a capacitor, and adjusting the voltage when it is over a certain pre-set amount; and f) connecting the capacitor to the DC output to filter out any pulse from an environment outside of the space between the positive and negative electrodes or from a circuit consisting of the converter, first detector, second detector, the microprocessor, and the pulse width modulator to ensure the DC output is DC.

BRIEF DESCRIPTION OF THE DRAWINGS

These and other features of the invention will become more apparent in the following detailed description in which reference is made to the appended drawings.

FIG. 21: It is a table of the results of harmonic analysis of fair weather atmospheric field at YBJ, Tibet. The phase of annual cycle in this table is October, and for accurately, it should be nearly at the autumnal equinox. The autumnal equinox is on September 22 to 24, and for simplicity, we use September 23, so the phase is 31+28+31+30+31+30+31+31+23=266.

DETAILED DESCRIPTION OF THE INVENTION

Figure 1:
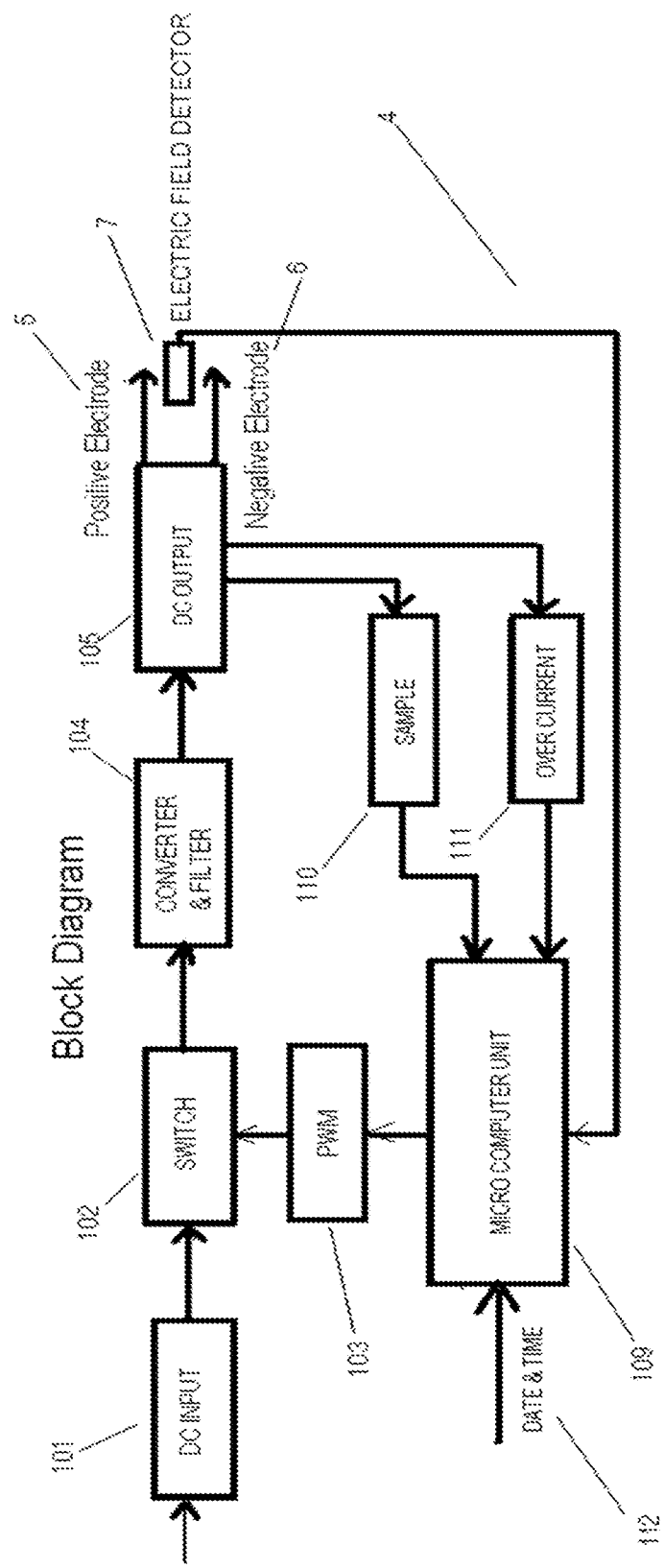
FIG. 1: Block diagram of the system according to the present disclosure providing a smooth (slowly fluctuating, no pulse), incrementally changing, positive DC electric field.

The present invention relates to the generation of wellness promoting, DC electric fields which simulate the strength, fluctuations and cycles (rhythms) of wellness promoting, natural electric fields in the environment. Whereas prior art was limited by the technology available at the time, the application of a microprocessor configured to direct the pulse width modulation of a DC output, and receive data from an electric field detector, allows for the real-time generation and control of wellness promoting electric fields in an environment in the vicinity of a subject.

Various features of the invention will become apparent from the following detailed description taken together with the illustrations in the Figures. The design factors, construction and use of the electric field generation (including modulation and simulation) system and methods disclosed herein are described with reference to various examples representing embodiments which are not intended to limit the scope of the invention as described and claimed herein. The skilled technician in the field to which the invention pertains will appreciate that there may be other variations, examples and embodiments of the invention not disclosed herein that may be practiced according to the teachings of the present disclosure without departing from the scope and spirit of the invention.

Definitions

Unless defined otherwise, all technical and scientific terms used herein have the same meaning as commonly understood by one of ordinary skill in the art to which this invention pertains.

The use of the word "a" or "an" when used herein in conjunction with the term "comprising" may mean "one," but it is also consistent with the meaning of "one or more," "at least one" and "one or more than one."

As used herein, the terms "comprising," "having," "including" and "containing," and grammatical variations thereof, are inclusive or open-ended and do not exclude additional, unrecited elements and/or method steps. The term "consisting essentially of" when used herein in connection with a composition, device, article, system, use or method, denotes that additional elements and/or method steps may be present, but that these additions do not materially affect the manner in which the recited component, device, apparatus, system, use or method functions. The term "consisting of" when used herein in connection with a component, device, apparatus, system, use or method, excludes the presence of additional elements and/or method steps. A component, device, apparatus, system, use or method described herein as comprising certain elements and/or steps may also, in certain embodiments consist essentially of those elements and/or steps, and in other embodiments consist of those elements and/or steps, whether or not these embodiments are specifically referred to.

As used herein, the term "about" refers to an approximately +/−10% variation from a given value. It is to be understood that such a variation is always included in any given value provided herein, whether or not it is specifically referred to.

The recitation of ranges herein is intended to convey both the ranges and individual values falling within the ranges, to the same place value as the numerals used to denote the range, unless otherwise indicated herein.

The use of any examples or exemplary language, e.g. "such as", "exemplary embodiment", "illustrative embodiment" and "for example" is intended to illustrate or denote aspects, embodiments, variations, elements or features relating to the invention and not intended to limit the scope of the invention.

As used herein, the terms "connect" and related derivatives refer to any direct or indirect physical association between elements or features of the system, apparatus and/or devices of the present disclosure. Accordingly, these terms may be understood to denote elements or features that are partly or completely contained within one another, attached, coupled, disposed on, joined together, etc., even if there are other elements or features intervening between the elements or features described as being connected.

As used herein, the terms "space" and "environment" refer to a defined volume in which objects, subjects and entities may exist, enter into or exit or be in the vicinity of. When referred to in relation to a subject, the subject may occupy a portion of the space, substantially all of the space or be in a space adjacent or proximal to the referred to space.

As used herein, the term "modulate" and related derivative terms, refer to the steps taken, result or effect of changing a condition, the parameters, or characteristics of an electric field generated by the system, existing in an environment, or of a signal or other output from the system of the present disclosure. The modulation of an electric field may be carried out in a manner that simulates the generation of naturally occurring, and in particular, wellness promoting electric fields. Modulation of an electric field generated by the system according to the present disclosure may include turning on and stopping the generation of a DC output, or varying the amount of the DC output. Alternatively, modulation of an actual or simulated electric field in an environment may refer to providing or introducing an electric field generated by the system of the present disclosure to create (generate) a fair weather or wellness promoting electric field in the environment. An electric field can be modulated in real-time, at set intervals or on a discretionary basis as determined by a subject or user of the system according to the present disclosure.

The terms "therapy" and "treatment," as used interchangeably herein, refer to an intervention performed with the intention of promoting good health and general wellness, as well as alleviating the symptoms associated with, preventing the development of, or altering the pathology of a disease, disorder or condition. Thus, the terms therapy and treatment are used in the broadest sense, and in various embodiments include one or more of the prevention (prophylaxis), moderation, reduction, and/or curing of a disease, disorder or condition at various stages. Subjects in need of therapy/treatment thus may include those already having the disease, disorder or condition as well as those prone to, or at risk of developing, the disease, disorder or condition and those in whom the disease, disorder or condition is to be prevented.

As used herein, the term "simulate" and related derivatives refer to the aspects of generating (including modulating) an electric field, which result in substantially similar rhythms, (e.g. intensities, strengths, fluctuations and/or cycles) as naturally occurring (e.g. atmospheric, biological, and geological) electric fields, or desired wellness promoting electric fields. The electric field output from a system and method according to the present disclosure may simulate a desired electric field or said output may result in the simulation of desired (effective) electric field in a target environment.

The terms "subject" as used herein refers to a human, non-human animal or plant.

The term "variable" as used herein refers to a non-constant electric field over a period of time. A smooth electric field may be a naturally occurring (slow fluctuating and/or cyclical) electric field, or an electric field produced or influenced by manmade constructions, such as built structures, transport means, electronic devices and synthetic chemical compositions (e.g. used in the making of utilitarian objects such as articles of clothing).

The term "wellness promoting" as used herein refers to electric fields which have the effect or result of improving the well-being of a subject.

The term "Pi" is "$\pi$", equal to 3.14169.

The term "dE" is changing of electrical field, the term "dT" is the changing of time.

The term "fair weather" is weather that satisfies the conditions set out in Xu, including, for example, the following conditions: (1) mean value of the electric field strength is between 0 V/m and 300 V/m; (2) The wind velocity at most 6 m/s; (3) The cloud cover in the sky occupy less than one octet of the perceptible whole sky; (4) the perturbation of the field intensity is within three times standard deviation; and (5) there are no plumes of smoke, dust storms, fog. If any one of these conditions are not satisfied over the course of an hour, the weather conditions of the hour are excluded from the wellness promoting or fair weather electric field simulation parameters. Similarly, when four consecutive hours of weather conditions are excluded for not meeting the criteria of fair weather, the conditions of the entire day are excluded. Additionally, fair weather conditions may be considered as wellness promoting when a subject's internal ion flow is consistently in one direction from a positive aspect to a negative aspect of the body. The present invention accordingly ensures ion flow in a subject is in a positive direction such that the ions do not reverse their flow, but many of the systems disclose by the prior art would cause ions to reverse their flow and thereby cause disruption to a subject's well-being. Aligning the ion channels with an electric field and keeping the ions in channels flowing in the same direction is very important because ions move in very small channels. Suddenly changing the electric field will let ions collide and react with each other, as well as with the surrounding protein and cells.

It is contemplated that any embodiment of the compositions, devices, articles, methods and uses disclosed herein can be implemented by one skilled in the art, as is, or by making such variations or equivalents without departing from the scope and spirit of the invention.

System for Generating a Smooth, Incrementally Changing Electric Field in Real-Time Certain embodiments of the invention relate to systems and methods for generating a desired wellness promoting, positive, variable electric field.

In one embodiment, the system is configured as a single device with various modules. In another embodiment the system is configured as a group of interconnected devices. The systems according to the disclosure is configured to apply DC to DC technology and integrates a microprocessor based feedback control system, comprising the following components: Power input, DC, date and time inputs, microprocessors, switches, voltage conversion and filtering, DC outputs coupled to electrodes, over current and/or over voltage detection, and pulse width modulation. The microprocessor controls the width of the pulse that turns the switches on and off, thus controlling the time of charge of a capacitance for the conversion of a low voltage to a higher voltage for outputting; With the help of R15 and R16 (FIG. 20), the microprocessor samples the output voltage through a feedback mechanism comprising an electric field detector to maintain and modulate the DC output in a stable and controllable manner.

Figure 19:
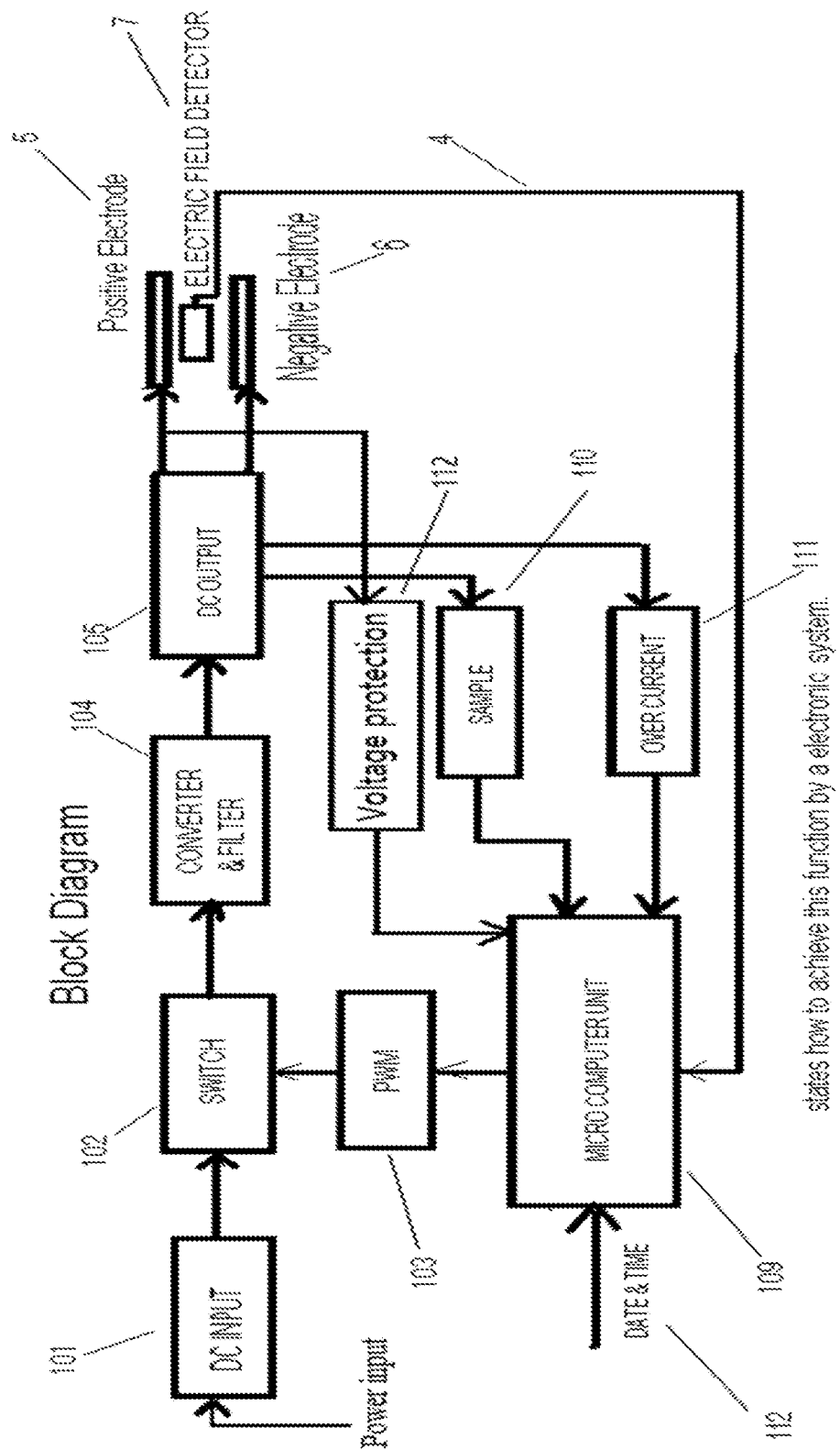
FIG. 19: A new block diagram of the system, base on FIG. 1, adding block of power input and voltage protection.

FIGS. 1 and 19 are block diagrams of generalized embodiments of the system according to the present disclosure, employing pulse width modulation and real-time control of a DC electric field output by a microprocessor based on the real-time monitoring of an actual (effective) electric field in a target environment. The microprocessor based control of the system in communication with the electric field detector, as well as current and voltage overage detectors is shown in greater detail FIGS. 4 and 20. As shown in FIG. 1, an exemplary system's architecture comprises an electric field generating sub-system and electric field control sub-system. The electric field generating sub-system receives a DC input from a power source, converts it to a DC output to generate an electric field in between a positive and negative electrode. The electric field control sub-system comprises an electric field detector which detects the actual electric field strength in the environment in between the electrodes and transmits this information to the microcomputer (microprocessor). The microprocessor conducts processing operations to determine the DC output required to modulate the DC electric field generated by the electric field generating sub-system.

Figure 5:
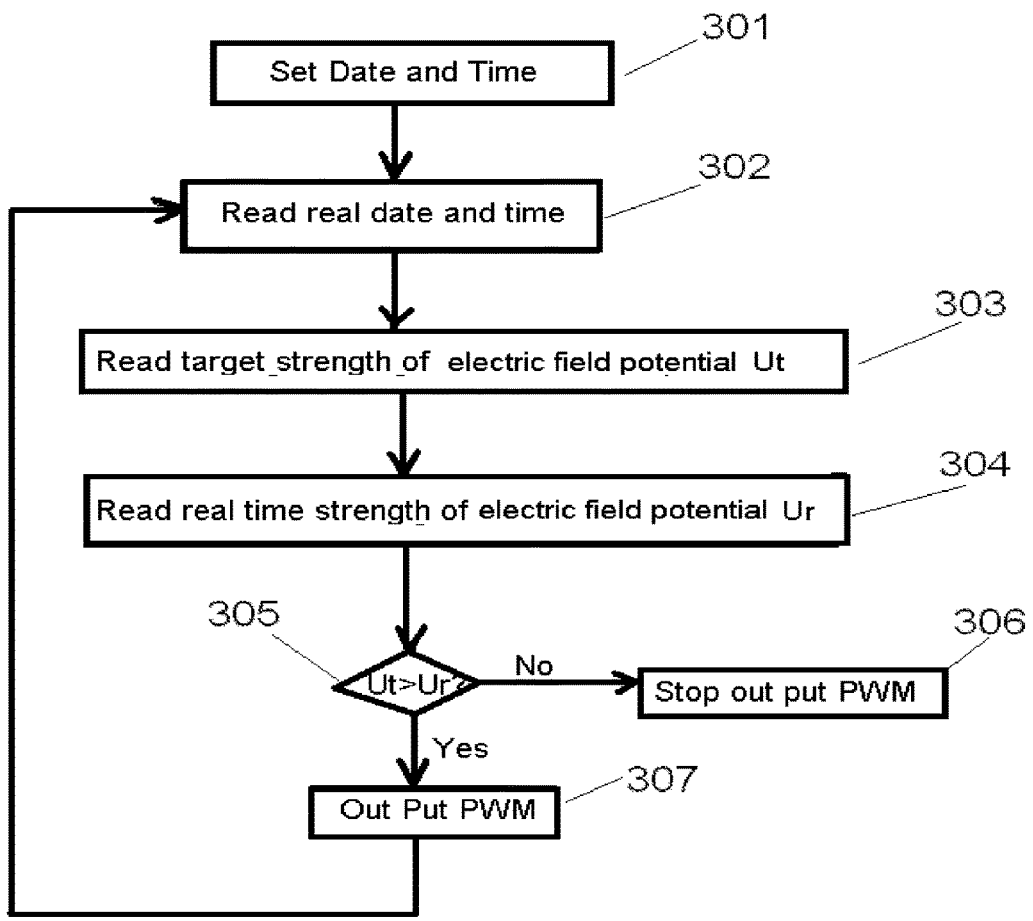
FIG. 5: An embodiment of the method of modulating a DC electric field according to the present disclosure including the steps controlled by the microprocessor of the system.
Figure 6:
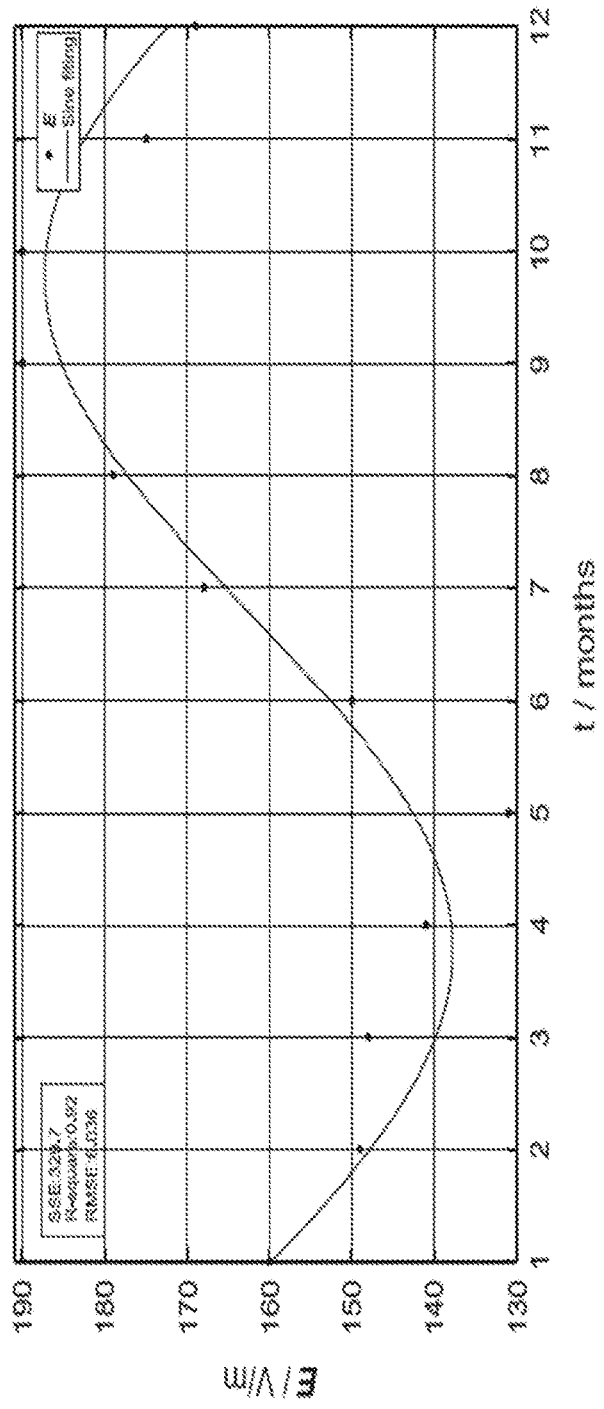
FIG. 6: Documented, yearly variation of atmospheric electric field in fair weather conditions at YBJ, Tibet (B. Xu et al., Journal of Atmospheric and Solar-Terrestrial Physics 97 (2013) 85-90), incorporated herein in by reference in its entirety. Only about 40% of the time are the conditions classified as fair weather in YBJ, which is a plateau with a lot sun. Other locations have fair weather for a much smaller percentage of time, as low as 5% with reference to the criteria used to categorize conditions as fair weather.
Figure 7:
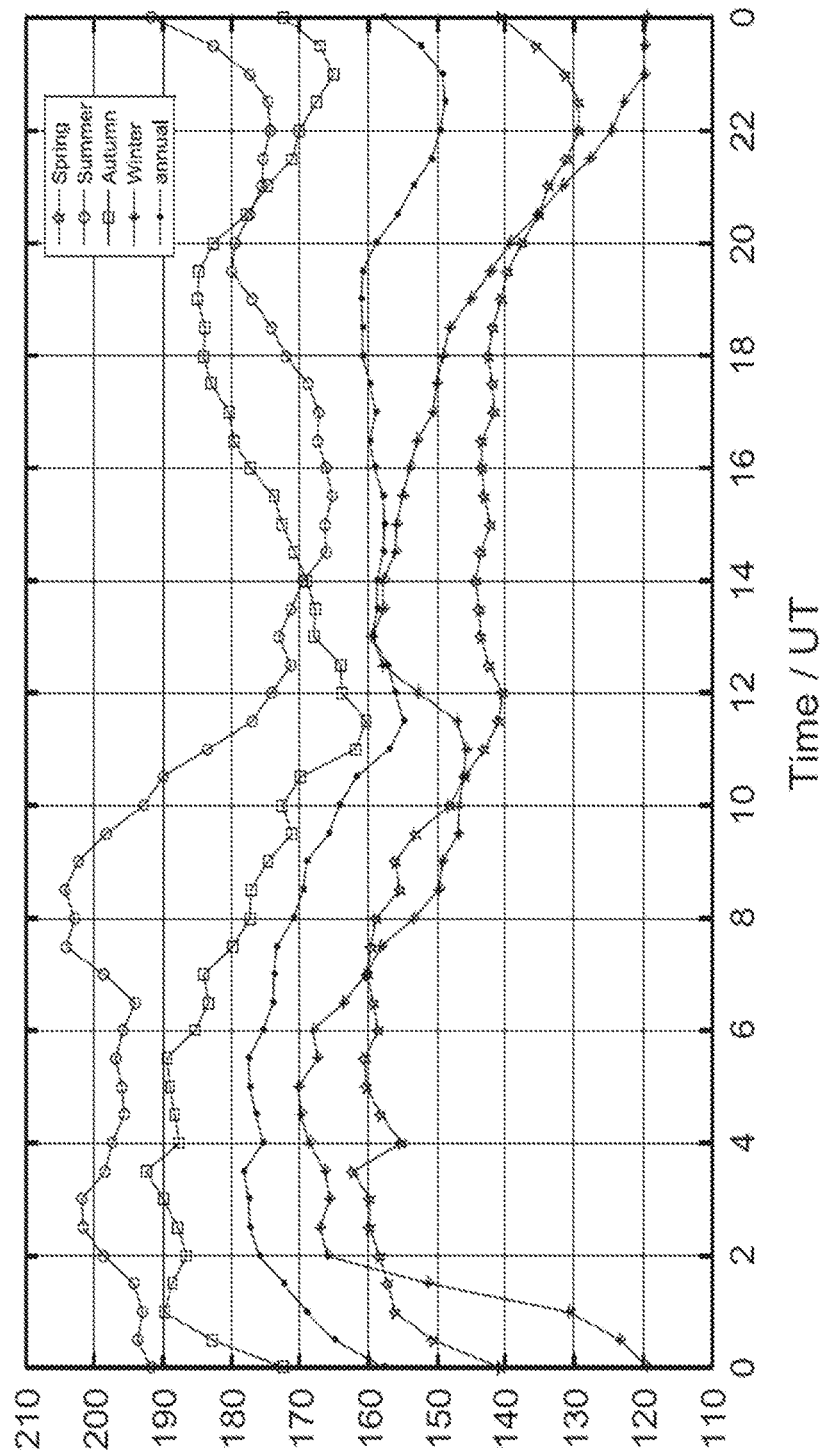
FIG. 7: Documented daily variation of atmospheric electric fields in fair weather conditions at YBJ, Tibet (B. Xu et al., Journal of Atmospheric and Solar-Terrestrial Physics 97 (2013) 85-90).
Figure 8:
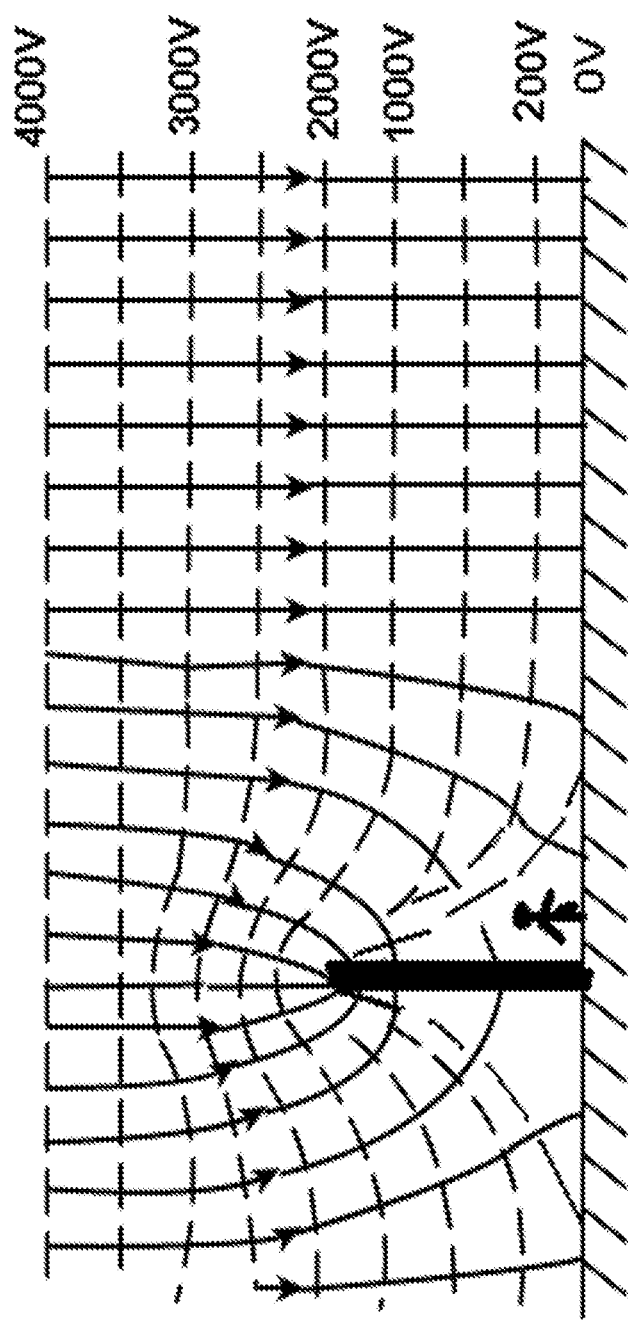
FIG. 8: Schematic representation of how a building, or other tall objects shield a subject or prevent a subject from being charged by the ionosphere (prior art, adapted figure).

FIG. 5 depicts the generalized embodiment of a method according to present disclosure for controlling the system of FIG. 1, with regard to the method sub-steps performed by the microcontroller. A microcontroller (e.g. in the form of a microprocessor in a computer) stores information and instructions relating to the strength of a desired wellness promoting, smooth electric field over time to be simulated over time in an environment and correlates this to the actual date and time input into the microprocessor for an existing (target or selected) environment to generate instructions for the simulation of such a natural, or well-being promoting electric field (e.g. using formulas to calculate the desired strength of the smooth electric field required based in part on date and time inputs).

A real-time clock is operatively associated with the microcontroller (microprocessor). The microcontroller reads the date and time and then retrieves the strength value of the smooth electric field desired, to create a DC output using PWM (Pulse Width Modulation). The PWM device turns a transistor on or off, to regulate the charging of the electric field generating subsystem and create (generate) an output by converting the DC input to a DC output discharged into an environment as an electric field between the positive and negative electrodes. This system also has a feedback loop mechanism between the microprocessor and electric field detector as exemplified in FIGS. 4 and 20. The microcontroller is operatively associated with an ADC (analog digital converter) to read the real (actual) strength of the electric field in an environment, and compare it with the target strength and other properties of the desired electric field to be simulated based, at least in part, on the date and time, and other input parameters. When the actual electric field reaches the desired strength or value, the microprocessor will stop the output of PWM and when the actual electric field falls below a desired value, the microprocessor will initiate PWM to increase the DC output. For the safety of subjects, the system can incorporate voltage and current overage protection mechanisms which will stop the DC output and generation of the associated electric field.

In one embodiment the microprocessor is configured with software, or programming instructions to receive information from a real-time clock, and other user inputs defining the parameters of a desired (wellness promoting) electric field. For example, once the date and time of the clock are set, the microcontroller will from time to time read the real date and time from the clock, then look up from a table of field strengths, or apply a formula (stored or accessible from the memory of the microcontroller) to access the characteristics and generate the instructions for simulating a desired smooth, incrementally changing electric field strength with reference to the date, time and other parameters.

With reference to FIG. 5, a target strength of a desired electric field Ut is compared to the read (detected and transmitted) actual (real-time) strength of the electric field in a target environment, Ur. If, once the microprocessor compares Ut and Ur, Ut>Ur, the microprocessor will send a signal to stop the pulse from the PWM device (module), or otherwise, send a prorated signal instruction in order to achieve the target strength of the desired electric field effected through the PWM device. This cycle of monitoring actual electric field strength, processing electric field data with reference to set parameters and sending instructions to modulate the electric field output of the system according to the present disclosure, may be carried out in real-time on a continuous basis, at pre-determined and relatively frequent intervals, and adjusted at selected times as needed, in order to simulate a wellness promoting electric field in a target environment.

Simulation of Wellness Promoting Electric Fields

To determine and generate the appropriate electric field outputs needed to effectively simulate wellness promoting (e.g. natural) variable electrical fields, beneficial to living beings, regular, or continuous (incremental, non-constant or variable) and smooth (slow fluctuating, no pulse) modulation of the DC output is required. In prior art such as FR976815, however, to the extent the generation of a positive electrostatic field is disclosed, it is substantially permanent (constant). Once the system and value for generation of an electric field output is set, no means is provided to adjust the electric field output with regard to any parameters which could affect the effective electric field in an environment on a given date, time (e.g. day or night), or season (e.g. winter or summer), etc. No change can be made to electric field output unless manually changed by the user. Moreover, the user is not provided with the means to optimize the settings that can be manually manipulated to produce the desirable rhythms in the electric field output in order to optimize said output and simulate a wellbeing promoting electric field.

Living beings subjected to a constant electrostatic field is against the natural conditions and environments that living beings have adapted to and evolved with for millions of years. Under fair weather conditions, which are favourable to living beings, the natural electric field changes over the day, daily, seasonally, annually, etc. At night is when natural electric fields tend to be at their lowest levels and more so at the time of the spring equinox, reaching as low as 100V/m. The highest levels or peaks for natural electric fields are generally in the morning of the fall equinox and could reach as high as 200V/m. (See "Periodic variations of atmospheric electric field on fair weather conditions at YBJ, Tibet", B. Xu et al., Journal of Atmospheric and Solar-Terrestrial Physics 97 (2013) 85-90).

Unlike FR976815 and other prior art, the present disclosure seeks to respect the natural electric field phases and how the minimum and maximum levels are linked to the solstices, equinoxes on an annual basis, and other aspects of the earth's natural cycles over the short and long term. The present disclosure also takes into account the qualities (e.g. Sine functions) of an electric field as it exists under good weather condition. This means that the field strength must change incrementally, slowly and without sudden fluctuations, in step with the rhythm and strength levels of daily, monthly, seasonal, yearly and other universal/planetary cycles, having cyclical fluctuations ranging, for example, between about 100 to 200, or between about 138 to 187.6 volts per meter, with daily highs around midday and daily lows around midnight. The cycle of the change as implemented by the system and methods of the present disclosure combines and optimizes electric field outputs with actual electric field conditions to simulate 15 minute, daily, yearly, multi-year cycles (e.g. 10, 12, and 180 year cycles) and other natural (wellness promoting), smooth and incrementally changing electric field cycles known in the art.

Weather conditions are closely related to the health condition of living beings. Under fair weather conditions, atmospheric electric potential (voltage) increases about 150 V/m when climbing against the gradient of the electric field. Under bad weather conditions, the electric potential (voltage) decreases, turns to negative, or rapidly changes. Given the evolution and acclimatization that creatures have been exposed to and adapted to for millions of years, a relatively stable atmospheric electric field (smooth and incrementally fluctuating) can be considered as beneficial for well-being. Smooth and continuous change in naturally occurring electric fields can be understood as a kind of tidal energy, which benefits living beings. Atmospheric electric fields are modulated weakly by various planetary/universal cycles, such as the solar diurnal cycle, annual cycle, monthly cycle, seasonally cycle, 10 yearly cycle, 12 yearly cycle, 60 yearly cycle, 180 yearly cycle, and 15 minute cycle.

Different locations have their own rhythm(s) (electric field fluctuation patterns and cycles). For example, when a city is very is close to the ocean, the rhythms of the local fair weather atmospheric electric fields are quite different from those inland, or on a plateau. Normally, at inland locations (e.g. in continent), the daily variation of electric fields has two peaks and two valleys, and seasonal variations. By contrast, locations close to the ocean, the Northern Arctic and Antarctica, have single peak and single valley electric field rhythms, with very little seasonal change, very similar as Carnegie curve.

Figure 9:
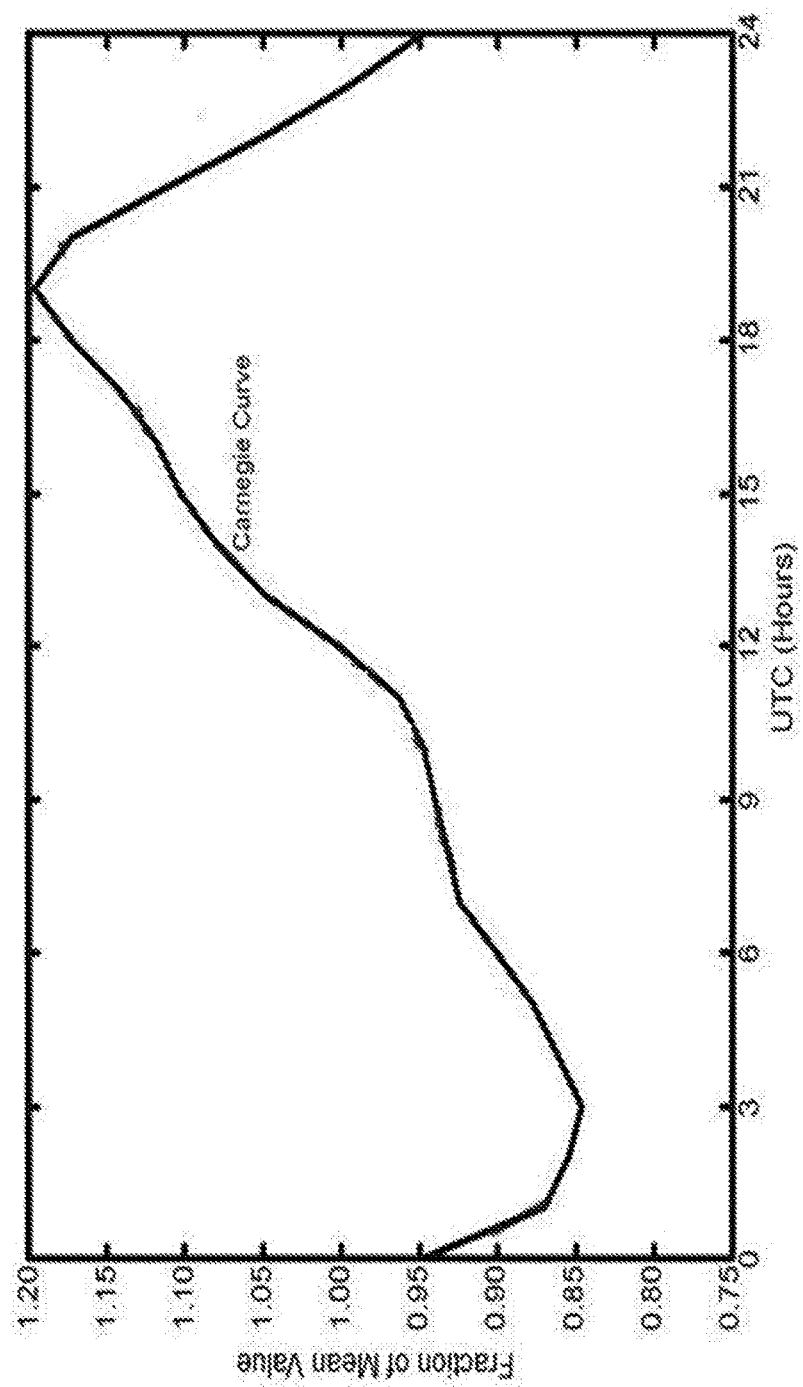
FIG. 9: Representation of Carnegie curve, i.e. the single diurnal cycle variation of the Earth's fair weather, atmospheric electric field in clean air (analogous to representation available from R. G. Harrision, Sury Geophys (2013) 34:209-232), incorporated herein by reference in its entirety.
Figure 10:
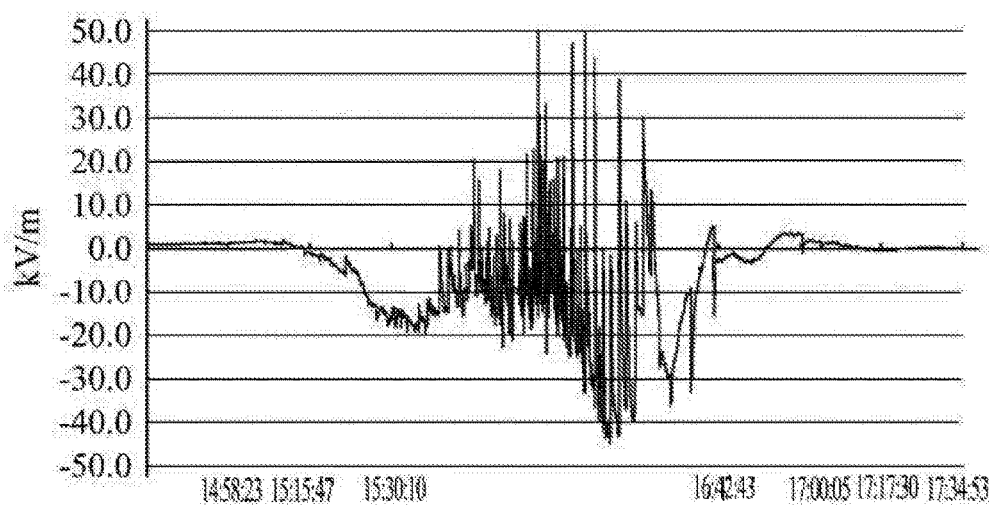
FIG. 10: Schematic representation of how a thunderstorm affects atmospheric electric field(s) (prior art).
Figure 17:
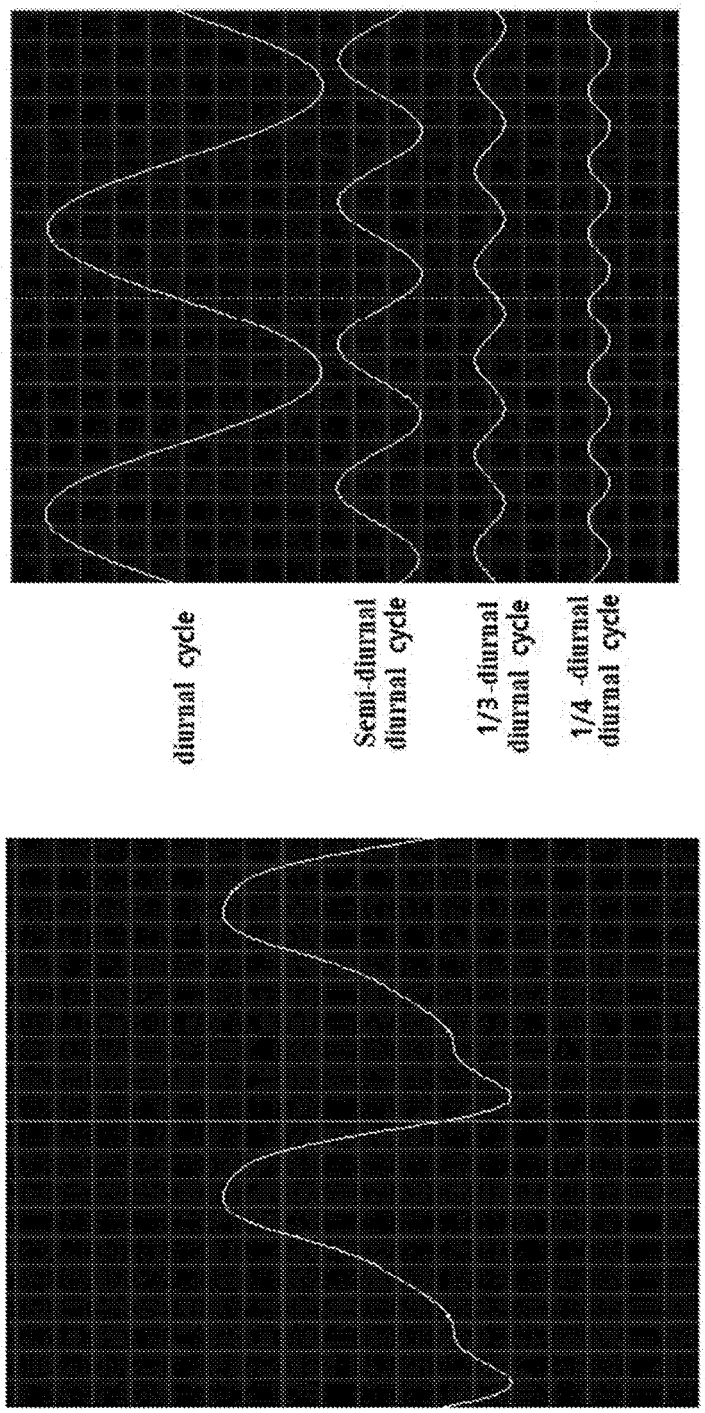
FIG. 17: It is a simulation figure from computer of daily variation of atmospheric electric field of Carnegie curve according some parameters in table 4 annual about amplitude and phase angle of from the article "The Carnegie Curve"[2] (Harrison2013_Article_TheCarnegieCurve, Sury Geophys (2013) 34:209-232, DOI 10.1007/s10712-012-9210-2). The right side are fitting curves of diurnal cycle, semi-diurnal cycle, ⅓ diurnal cycle and ¼ diurnal cycle. The left side is the result of the combination of four harmonic component fitting curves. Start from UT 0:00 in the X-axis, and the strength of electricity is shown on the Y-axis. In this case, when applying the figure to a different location, we do not need to convert the UT (universal time) to local time because no matter where the location is, or what season it is, the Carnegie Curve has very little change.
Figure 18A:
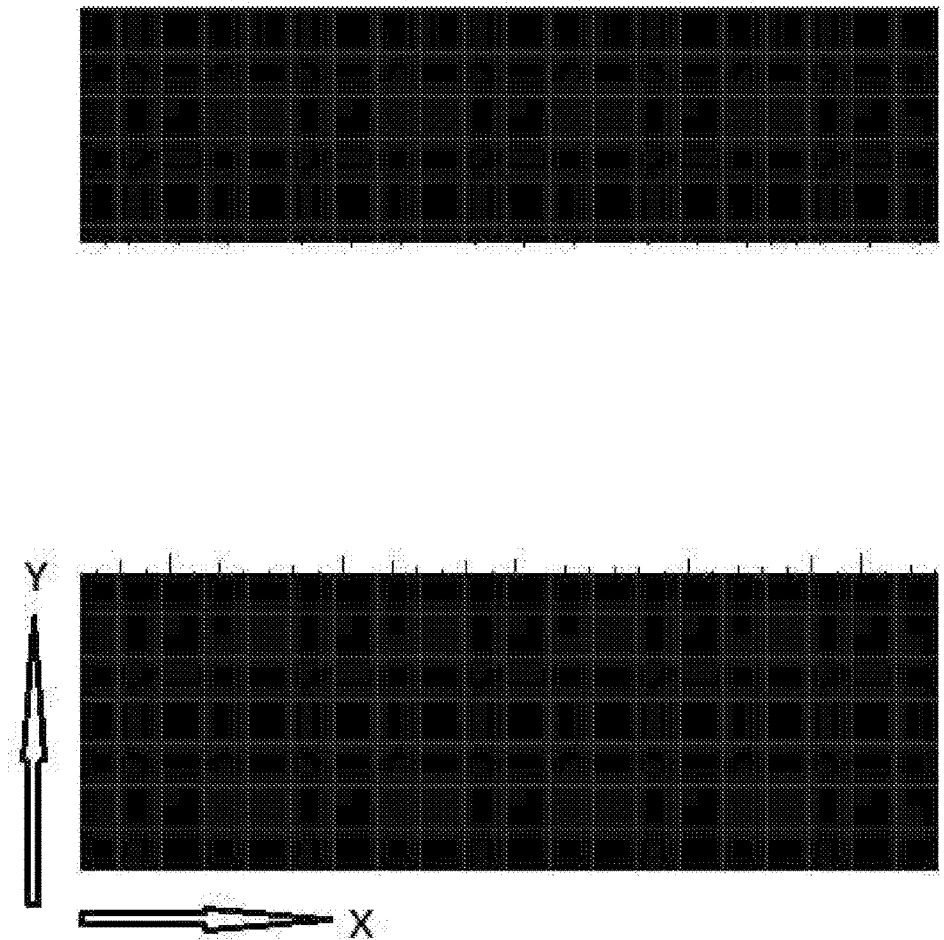
FIG. 18: (a) is a simulation figure from computer of yearly variation of atmospheric electric field in fair weather conditions about oceans according some parameters from the Harrison article. It looks like a straight ribbon with the indicated amplitude. In (b) 4 harmonic competent fitting curves look like straight ribbons also. If we want to know how they look like in the real time, we can zoom into a very short moment, such as 2 days, and they look like FIG. 17.
Figure 18:
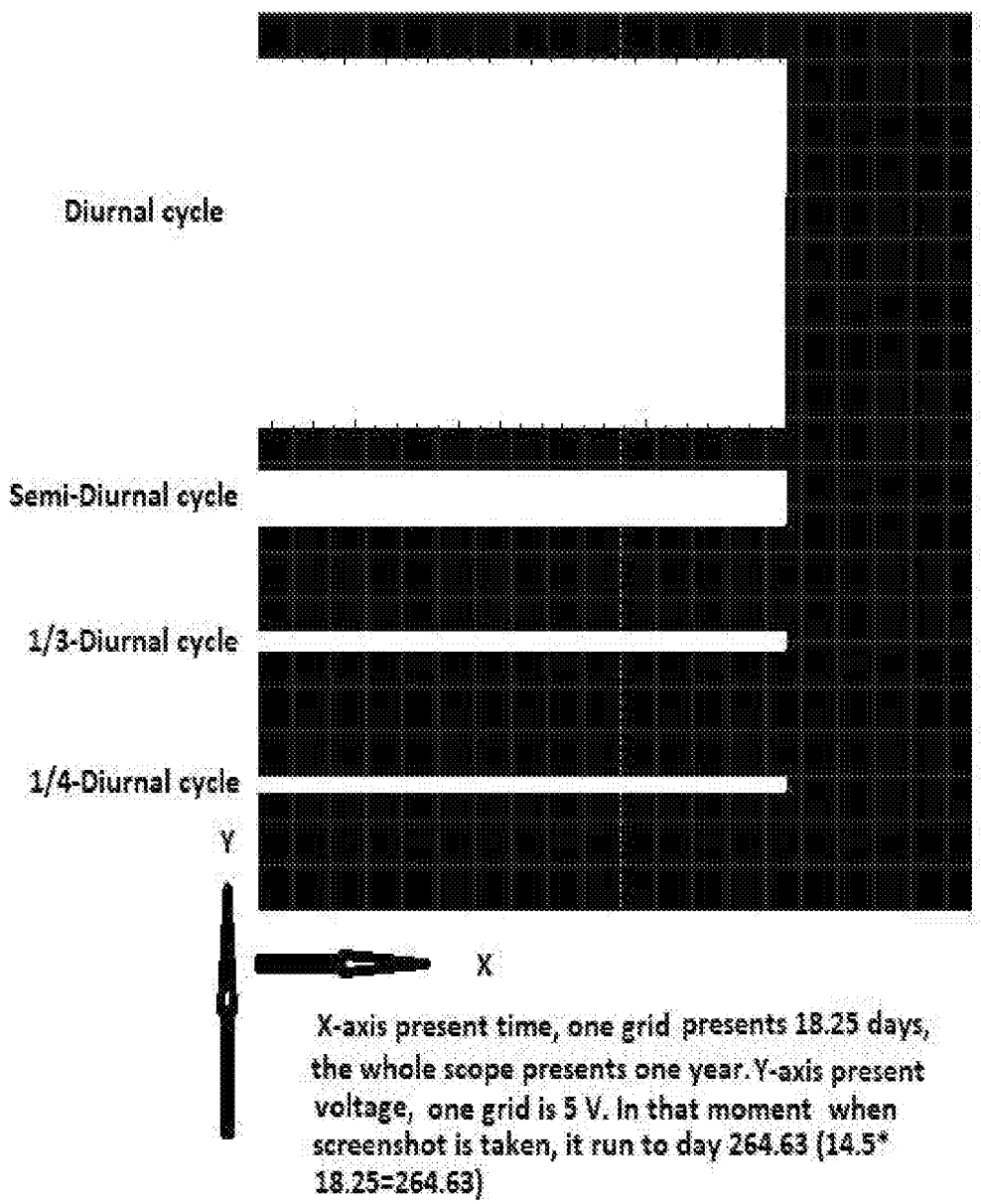

FIGS. 6, 7, 15 and 16 show the rhythm of the atmospheric electric fields of Tibet, a very high altitude plateau. There are two peaks and two valleys. These two figures show not only the daily change, but also the seasonal change. This is an ideal E (electric field) rhythm of inland. The Carnegie curve (see FIGS. 9, 17 and 18) shows a special fair weather atmospheric electric field rhythm from the ocean, there is only one peak and one valley.

By simulating, fair weather atmospheric electric fields which have a relatively slow fluctuating (non-constant/variable), no pulse (smooth) rhythm, such as those fields which exist in locations where there is a lower occurrence of diseases, or where individuals have a longer life span, the wellbeing of a subject can be supported. The systems and methods of the present disclosure provide this capability. For example, if there is a city, where a cancer patient lives there for a while, and are able to heal by themselves, this may be an indicator of a good rhythm which can be simulated according to the present disclosure. The Carnegie curve also represents a good electric field rhythm, given that all beings evolved from the ocean. In other words, certain natural and regionally occurring rhythms may be more or less naturally aligned with a subject's biological and physiological make-up. The Carnegie curve rhythm may be a natural bio chronometer human subjects are adapted to respond too since we evolved from ocean systems.

In certain embodiments, the system and methods of the present disclosure seek to simulate such beneficial (fair weather) inland and ocean electrical field rhythms, using processing protocols that leverage parameters from Xu and Harrison.

For the inland rhythm, we are going to get the ideal E reading by every second. Cosine is equal to Sine with a ½ Pi delay. For simplicity we use cosine instead of sine here to match the Xu article. We can derive the annual variation from FIG. 6, to determine that the axis of this cosine is between the highest E value of 187.6 and lowest E value of 138: (187.6+138)/2=162.8, the amplitude=(187.6−138)/2=24.8 V/m, and this amplitude matches the annual amplitude in FIG. 21 which is 24.8 V/m. The maximum nearly coincides with the autumnal equinox, where the Phase (time shift invariant)=266. So the annual variation=162.8+24.8*COS((day in the year 266)*2Pi/365). FIG. 21 indicates the fitting parameters of solar diurnal variation, semi-diurnal, 3rd harmonic and 4th harmonic variation components. By combining all amplitude and phase, we can derive strength of E=162.8+(24.8*COS(day in the year−266)*2Pi/365)+9.7*COS((second in the day by hour format−6.5)*2Pi/24)+6.6*COS((second in the day by hour format−5)*2Pi/12)+4*COS((second in the day by hour format−3)*2Pi/8)+3.3*COS(second in the day by hour format−2.3)*2Pi/6; Here are three exemplary derivations:

| Time | Day in year | Second in the day on Hour format | Detail in the formula | Total (V/m) |
|---|---|---|---|---|
| UT 23:21:39 of Feb. 27 | 58 | 23.361 | 162.8 + (24.8 * COS(58 − 266) * 2Pi/365) + 9.7 * COS ((23.361 − 6.5) * 2 Pi /24) + 6.6 * COS((23.361 − 5) * 2 Pi /12) + 4 * COS((23.361 − 3) * 2 Pi /8) + 3.3 * COS((23.361 − 2.3) * 2 Pi /6 | = 162.8 − 24.448 − 2.848 − 6.482 − 4.224 − 3.265 = 123.23 |
| UT 23:01:03 of Mar. 24 (about local per-sunrise hours) | 83 | 22.017 | 162.8 + (24.8 * COS(83 − 266) * 2Pi/365) + 9.7 * COS ((23.008 − 6.5) * 2 Pi /24) + 6.6 * COS((23.008 − 5) * 2 Pi /12) + 4 h * COS((23.008 − 3) * 2 Pi /8) + 3.3 * COS ((23.008 − 2.3) * 2 Pi /6 | = 162.8 − 24.799 − 3.708 − 6.600 − 4.400 − 3.860 = 120.13 |
| UT 3:30:05 of Sep. 23 | 266 | 3.5014 | 162.8 + (24.8 * COS(266 − 266) * 2Pi/365) + 9.7 * COS ((3.5014 − 6.5) * 2 Pi /24) + 6.6 * COS((3.5014 − 5) * 2 Pi /12) + 4 * COS((3.5014 − 3) * 2 Pi /8) + 3.3 * COS((3.5014 − 2.3) * 2 Pi /6 | = 162.8 + 24.8 + 6.862 + 4.670 + 4.063 + 1.646 = 204.54 |

Note that in the formulas presented the symbol '*' denotes a multiplication operation.

After combining annual variation and diurnal, semi-diurnal, 3rd harmonic and 4th harmonic variations, the daily curve shows 2 peaks and 2 valleys.

For the Carnegie curve rhythm, we can do the same as above. We use Sin to match the Harrison article. E=132.2+20.4 Sin(t/24*360−191.2)+6.1 Sin(2t/24*360−239.2)+2.2 Sin(3t/24*360−193.7)+1.6 Sin(4t/24*360−344.1), t is the time in the day in hour format as above. Some examples are provided in the table below:

| Time | Second in the day on Hour format | Detail in the formula | Total (V/m) |
|---|---|---|---|
| UT 3:02:00 | 3.0333 | 132.2 + 20.4Sin(3.0333/24 * 360 − 191.2) + 6.1Sin(2 * 3.0333/24 * 360 − 239.2) + 2.2Sin(3 * 3.0333/24 * 360 − 193.7) + 1.6Sin(4 * 3.0333/24 * 360 − 344.1) | = 132.2 − 18.914 + 3.163 − 1.334 + 1.593 = 116.71 |

-continued

| Time | Second in the day on Hour format | Detail in the formula | Total (V/m) |
|---|---|---|---|
| UT 17:02:30 | 17.0417 | 132.2 + 20.4Sin(17.0417/24 * 360 − 191.2) + 6.1Sin(2 * 17.0417/24 * 360 − 239.2) + 2.2Sin(3 * 17.0417/24 * 360 − 193.7) + 1.6Sin(4 * 17.0417/24 * 360 − 344.1) | = 132.2 − 20.395 + 5.824 + 2.170 + 1.593<br>= 162.18 |
| UT 7:10:05 of | 7.1681 | 132.2 + 20.4Sin(7.1681/24 * 360 − 191.2) + 6.1Sin(2 * 7.1681/24 * 360 − 239.2) + 2.2Sin(3 * 7.1681/24 * 360 − 193.7) + 1.6Sin(4 * 7.1681/24 * 360 − 344.1) | = 132.2 15 − 18.569 + 5.047 − 0.126 + 1.593<br>= 120.14 |

Factors and Parameters for Simulation of Wellness Promoting Electric Field by the Control Subsystem As provided herein, a microcontroller in the system according to the present disclosure is used to control strength of a DC electric field output and, as a result, the characteristics of the effective (actual) electric field in a target environment for the benefit of a subject. Using the system architecture and/or methods according to the present disclosure (e.g. as exemplified in FIG. 1), a DC electric field can be created (generated), which results in the simulation of a natural, desired or otherwise wellness promoting electric field in the environment, and to support the well-being of a subject.

There are a number of factors to be considered in order to design a system and in particular the control subsystem, able to modulate an electric field output according to the present disclosure.

One set of factors to be accounted for as part of the microprocessor's function in response to information received from the feedback mechanisms of the system according to the present disclosure, is how the ratio of three key resistances may change. These three resistances are: the resistance of a subject, the resistance of the gap between a space boundary (e.g. the ceiling of a room and subject, and the resistance of the power source (e.g. battery). The ratio changes whenever the temperature, humidity, wind, or chemical content in the air change. Any resistance changes, and the ratio will change, which is often. Modulation of the DC output accounting for these changes is achieved using the electric field detector in communication with the microprocessor according to the present disclosure by way of a feedback mechanism/circuit or subsystem created.

In one embodiment, the system of the present disclosure is configured to generate a slowly fluctuating, no pulse, (DC) positive electric field. The electric field generated is largely, or in part, the result of generating a certain strength of a DC electric field using the system according to the present disclosure in an environment. The environment may be, e.g. in a room in the vicinity of, or at the surface of various materials/structures, like a wall, bed, ceiling/roof, floor, chairs; in a car (and other transport means), around or in the proximity to footwear, headwear, gloves, other clothing and insole.

In another embodiment, the system is configured to generate a slowly fluctuating, no pulse, positive electric field using an integrated architecture of electric field generation, detection and control modules to deliver a desired strength of a DC positive electric field in an environment. The environment may be, e.g. in a room, in the vicinity of, or at the surface of various materials/structures, like a wall, bed, ceiling/roof, floor, chairs; in a car (and other transport means), around or in the proximity to footwear, headwear, gloves, other clothing and in soil. The electric field detection and (PWM) control modules ensure the electric field characteristics (e.g. strength) and by extension the effective electric field in an environment, can be maintained at and modulated to desired target strengths, substantially in real time, according to parameters accessible to the microprocessor of the control module, for simulating a wellness promoting electric field.

In still a further embodiment, the system also comprises voltage and/or current overage safety modules. Such safety modules will comprise their own detectors for monitoring voltage and current levels respectively. In a related embodiment, the over current protection threshold for triggering the microprocessor to stop the output of a DC electric field is set at less than 10 MA per subject. In another related embodiment, the over voltage protection threshold for triggering the microprocessor to stop the output of a DC electric field is set at 300 V/m.

In yet another embodiment of the system, a slowly fluctuating, no pulse, positive electric field is modulated to simulate natural electric field cycles, such as solar diurnal, annual, monthly, seasonal, 10 year, 12 year, 60 year, 180 year and 15 minute cycles. In a related embodiment the natural electric field cycle simulated follows the Carnegie curve. In a further embodiment, the natural or wellness promoting electric field cycle simulated follows a single diurnal cycle variation with a maximum of about 19 UT and minimum of about 03 UT.

In still another related embodiment, the natural or wellness promoting electric field cycle simulated is a fair weather cycle as has been or may be recorded anywhere in the world. Exemplary fair weather electric field cycles may include those which are experienced by subjects as preferred travel destination sites.

Other factors which may influence the selection of the natural electric fields to simulate for the wellbeing of a subject include the medical history of the subject, genetics and ancestry, and the environments that the subject developed in, or has been accustomed to living in, such as near the sea, or ocean at sea level, inland in relatively dense vegetative or forested regions, in desert regions, or in the mountains at high altitudes.

Additional factors that may impact the selection of desirable wellness promoting electric fields to simulate for the wellbeing of a subject, include the subject's typical living (awake/sleep) patterns and conditions, work patterns (day-time versus nocturnal worker), diet, types of physical activities or lack thereof, and likelihood of exposures to disruptions or negative electric fields which harm the wellbeing of a subject.

For the purposes of modulating the electric field output of the systems and methods according to the present disclosure, the presence of such factors must be accounted for in conjunction with influences on the effective electric field caused by universal and planetary forces at different locations (e.g. near the equator, towards the poles of the northern and southern hemispheres), the introduction of manmade infrastructures, macro and micro climates, shifts in the jet stream and ocean forces. The effective electric field feedback and modulation solution provided by the control subsystem of the present disclosure provides an efficient way to account for a multitude of variables and conditions.

Electrode Design and Placement for Simulation of Wellness Promoting Electric Fields Further requirements to effectively generate a desired electric field in an environment for the benefit of a subject relate to the placement of the negative and positive electrodes relative to the appropriate body parts of the subject. Failure to ensure proper electrode placement (positioning) or positioning of a subject relative to said electrode placements, can negate beneficial field effects, or even result in harmful effects on a subject. In expired patent FR976815, consideration of these factors is not stated or taught. Moreover, the teaching directs the skilled technician to apply the positive electrodes to the abdomen and the negative electrodes to the back of a subject. As shown in FIG. 1 of FR976875, the human subject would experience the application of a negative electric field when the system disclosed herein is installed for a bed. Before and as humans evolved from other primates, the back was towards the sky, and the feet and hands touched the ground. The FR976875 patent, however, discloses a configuration for generating an electric field that is opposite, or contrary to the environment, nature and context of human evolution, and therefore not configured to promote the wellness of humans.

Figure 2:
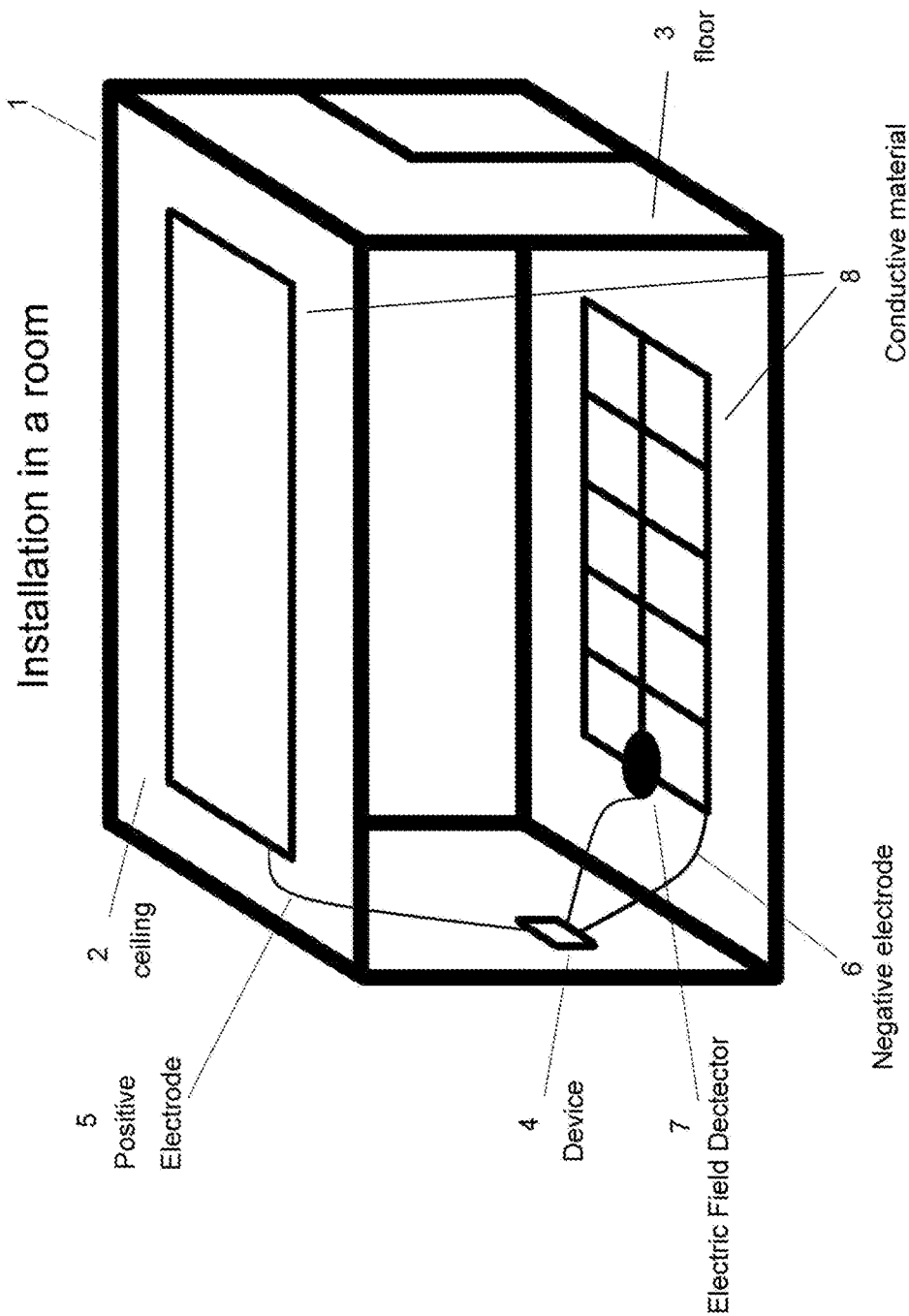
FIG. 2: Application of the system according to the present disclosure in a room. The system is configured to use the floor and ceiling of the room for the placement of the electrodes. A subject entering and sitting in the room would be positioned such that the positive electrode is closer to the head of the subject, and the negative electrode is closer to the feet of the subject.
Figure 3:
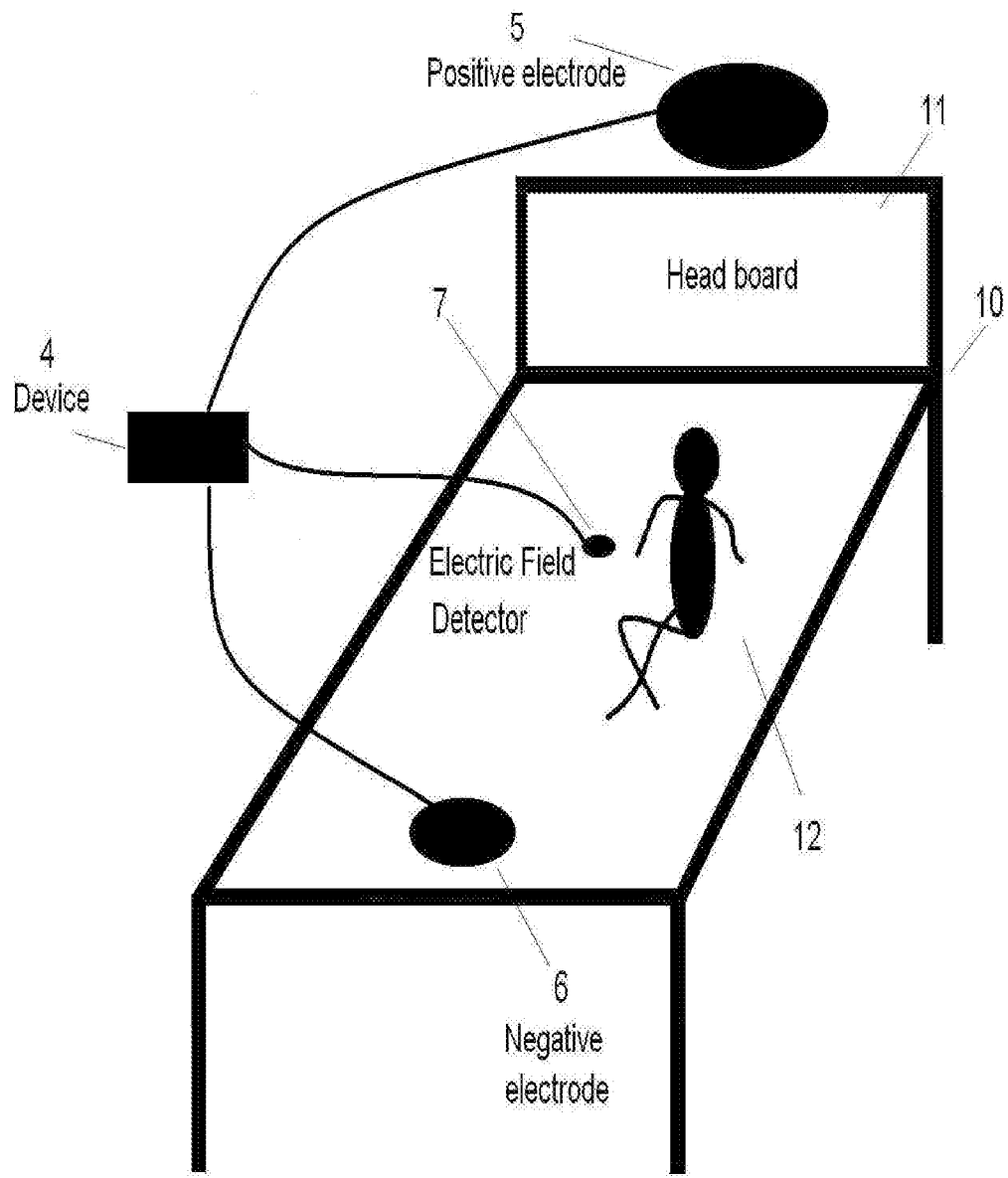
FIG. 3: Application of the system according to the present disclosure to the environment around or proximal to a bed. The positive electrode is positioned close to head, and negative electrode close to the foot of a subject.
Figure 11:
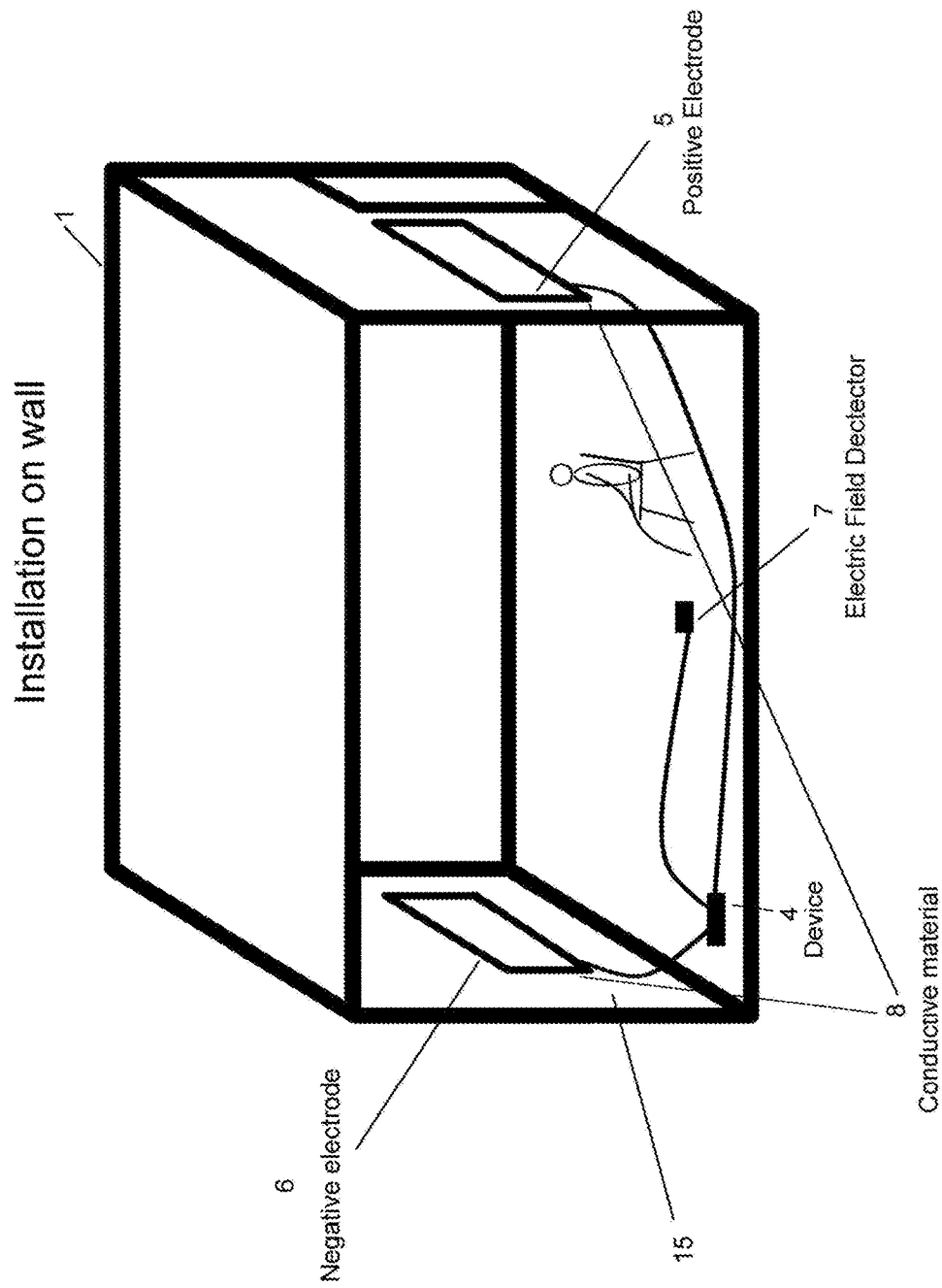
FIG. 11: Application of the system according to the present disclosure configured to use the walls of a room for the placement (positioning) of the electrodes and positioning of a subject. The positive electrode is closer to back of the subject, and the negative electrode is closer to the front or abdomen of the subject.

By contrast, the systems and methods of the present disclosure are configured to position the positive electrode close to a positive part of a living being and the negative electrode close to a negative part of the living being. For (human and non-human) animals the parts of the body oriented towards the sky are positive and the parts of the body oriented towards the ground are negative, e.g. when the position of the back is towards the sky, and the foot/paws or hands touch or point towards the ground. Similarly, for the purposes of electrode/subject alignment according to the present disclosure, a dorsal (posterior) part is positive compared to the ventral (anterior) part of the torso of a subject, which is negative. The head is generally a positive part compared to the rest of the body, whereas the feet and hands are negative parts compared to the rest of body. Accordingly, in FIG. 3 where the subject (12) is lying on a bed (10), the positive electrode (5) is positioned at, or in the vicinity of the bed headboard (11) proximal to the head of the subject (12) and the negative electrode (6) is positioned at the opposite end of the bed proximal to the feet of the subject. The microcontroller is housed in a separate unit (4) and operatively connected to the electric field detector (7) positioned in between the positive and negative electrodes proximal to the subject. In alternative embodiments shown in FIGS. 2 and 11, the electrodes are positioned on space boundaries of the enclosure (room) (1) in which a desirable electric field is to be generated. For example, in FIG. 2, the positive electrode is on the ceiling (2) of the room (1) and the negative electrode is on the floor (3), each contacting conductive material (8) affixed to these surfaces. In FIG. 11, the conductive material is affixed to the walls (15) to accommodate the positioning of the electrodes relative to the subject.

For botanical subjects (i.e. plants) leaves and stem are positive parts relative to the roots which are negative parts for the purposes of positioning the positive and negative electrodes of the system, respectively to generate a wellness promoting electric field.

In one embodiment of the system, the electrodes contact (touch) the subject in the environment where the electric field generated by the system is output. In another embodiment of the system, the electrodes do not contact the subject. The electrodes of the system can be formed in a variety of shapes and with a variety of conductive and semi-conductive materials. In an embodiment, one or both of the electrodes can be covered with a woven material to provide some protection from electric shocks when the electrode contacts the outer tissue layer of a subject. In another embodiment, the electrodes can be a triangular shape, annular shape, an elliptical ring shape or a cylindrical shape. In a further embodiment, the electrodes can be made of copper, aluminum, of a conductive fabric or similar semi-conductive materials.

Figure 12:
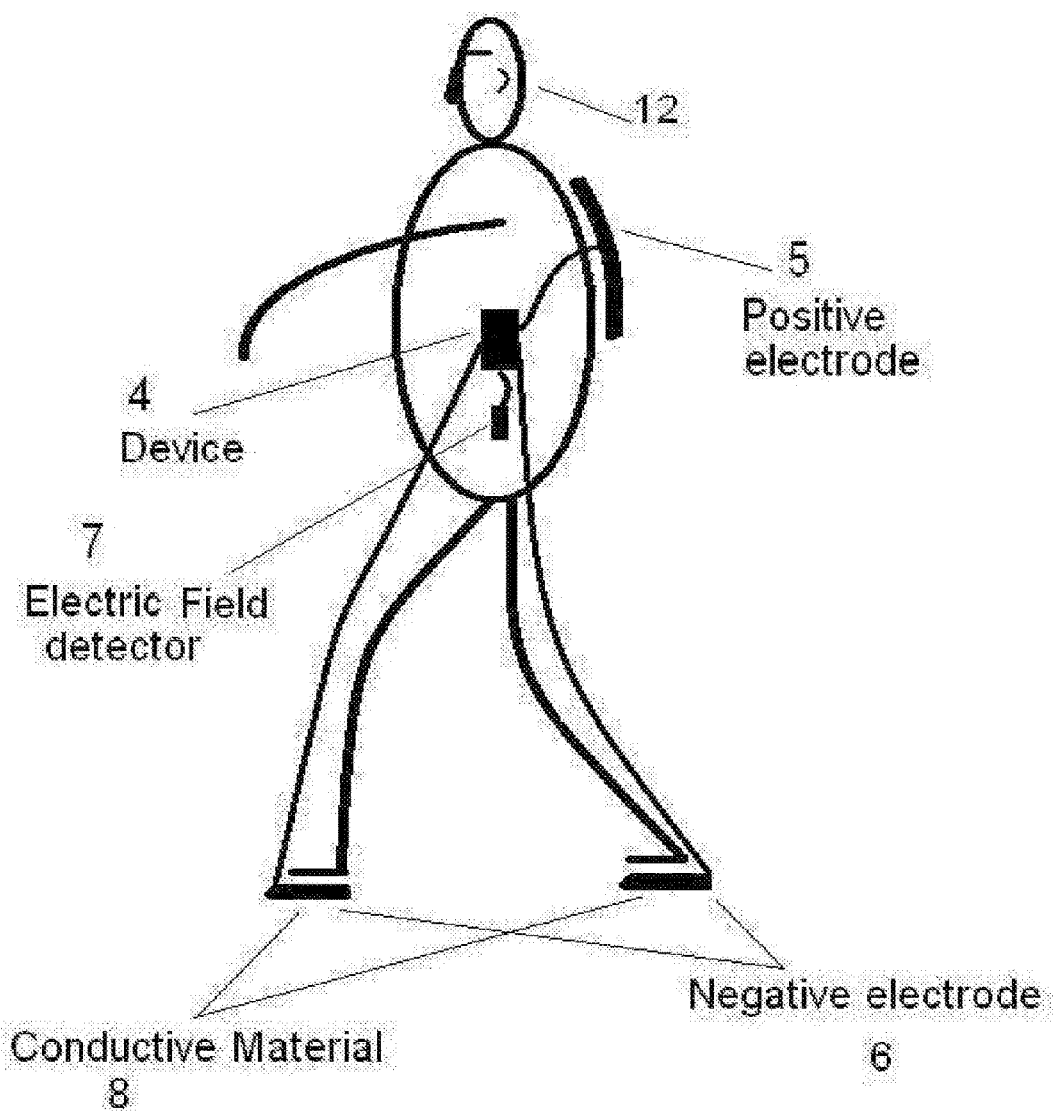
FIG. 12: Application of the system according to the present disclosure configured to generate an electric field around or proximal to wearable items. For the subject wearing the clothing or apparel, the positive electrode is positioned closer to back, and the negative electrode closer to foot of the subject.

In a further embodiment of the system, the electrodes are positioned for the positive electrode to be proximal to, or contact a positive part of a subject and the negative electrode is positioned to be proximal to, or contact a negative part of subject. A positive part of a subject is generally a part typically oriented towards the sky and a negative part of subject is generally a part typically oriented towards the ground, and may depend in a given situation on whether the subject is an upright position (sitting and standing) versus lying down. In another embodiment the positive part of a subject is the head, back (as shown in FIG. 12) or torso and the negative part of a subject is a hand or foot (as shown in FIG. 12). When the electrode is contacting the body of the subject (as shown for the back of the subject in FIG. 12), a woven cloth (9) may be used between the electrode and skin to provide some protection from electric shock to the skin tissue.

In the case of a botanical (plant) subject, the normal growth orientation is for the leaves and stem to be generally oriented towards the sky, and the roots to be oriented towards, or into the earth. This orientation corresponds generally to the positive and negative parts of the subject, respectively, and therefore the positive electrode of the system is positioned proximal to the leaf/stem of the plant and the negative electrode positioned proximal to the roots of the plant.

In the case of a non-human animal, the positive electrode is positioned proximal to the posterior (back) or head of the animal and the negative electrode would be positioned proximal to the feet or appendages of the animal in light of its typical stance or orientation when awake.

When a subject is in a room, standing, supported on a bed, in a chair or in a car and other transport means, the positive electrode is positioned proximal to the head of the subject and negative electrode proximal to the feet or any other lower part (closer to the ground) of the subject.

In one embodiment, when installed on the walls of a room, the positive electrode is positioned on the wall close to the back of the body of the subject, and the negative electrode is positioned to the wall close the abdomen of the body of the subject.

In one embodiment of the system, the DC electric field generated is less than 300 V/m. In a related embodiment, the electric field simulated by applying the system of the present disclosure is at all times less than 300 V/m. In related embodiments, the electric fields generated or effectively simulated by the system are between about 100 to about 200 V/m. In other embodiments, the electric fields generated or effectively simulated by the system vary by about 150 V/m over a period of time. In still further embodiments the electric fields generated by the system or effectively simulated by the system range in strength between 103V/m and less than 300 V/m. In alternative embodiments the electric fields generated or effectively simulated by the system range in strength between 105V/m and less than 300 V/m.

Applications of the System and Methods to Modulate an Electric Field

The systems and methods (processes) of the present disclosure may be used for the benefit of human and non-human animals and plants to enhance well-being and healing processes.

In one embodiment a method or process using the system according to the present disclosure for generating a positive electric field in a space, is carried out to support the wellness of a subject. The process/method comprises generating a target strength of a DC electric field output and positioning the electrodes of the system on the walls, floor or ceiling of a room, on an article of furniture, on an article of clothing or to the subject.

In an embodiment, when the electrodes are not contacting a subject, but are instead positioned at the boundaries of a space, such as the walls, floor, ceiling of a room, other enclosure (e.g. manmade bubble), the positive electrode is connected to conductive/semi-conductive material at said space boundaries, proximal to the head or back and the negative electrode is connected to conductive/semi-conductive material at said space boundaries, proximal to the feet or abdomen of the subject.

Figure 13:
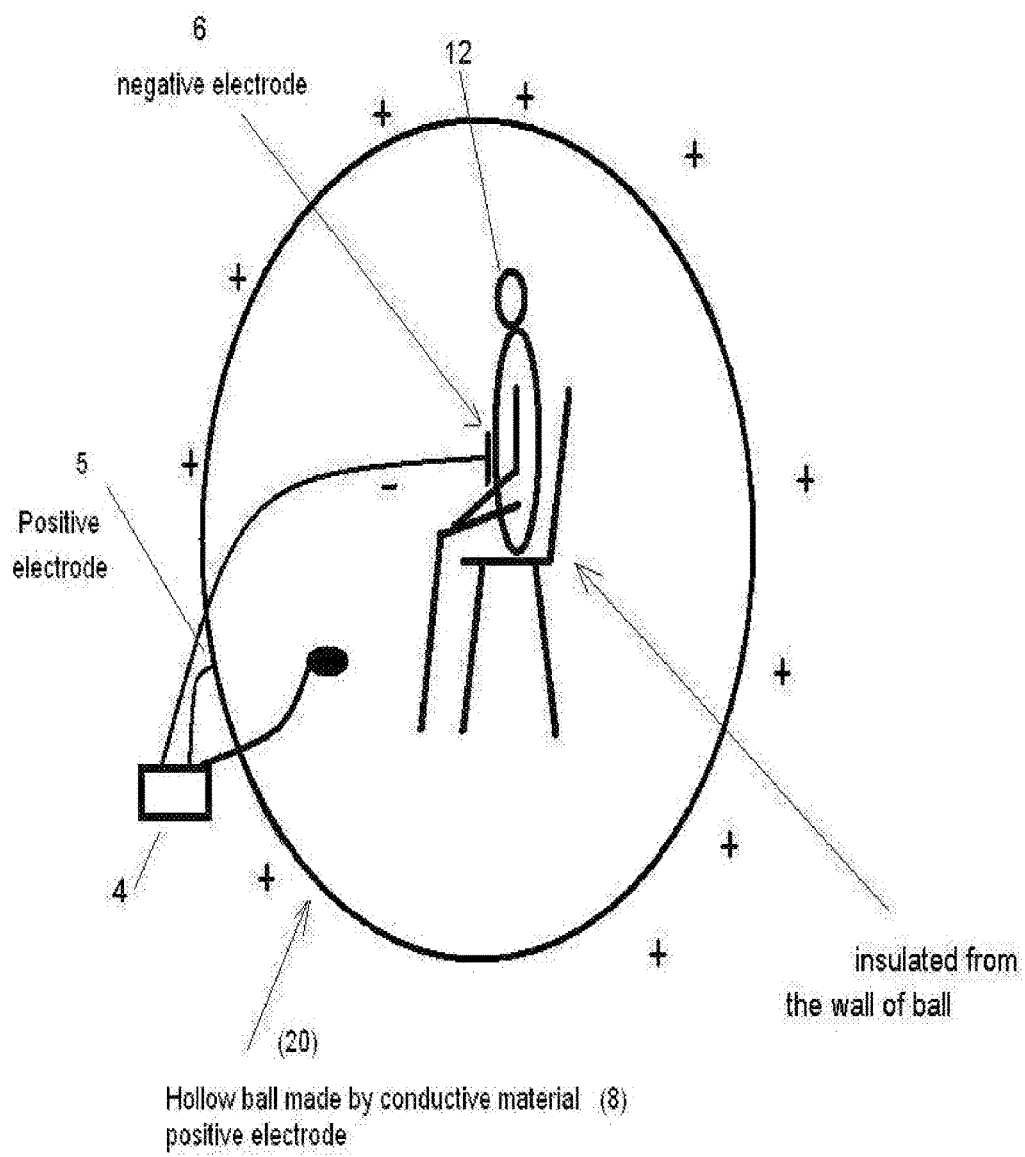
FIG. 13: Application of the system according to the present disclosure configured to generate an electric field within a bubble enclosure made of conductive material for the benefit of a subject. The positive electrode is positioned on the interior wall of the enclosure and the negative electrode is positioned on the front/abdominal part of the torso of the subject.
Figure 14:
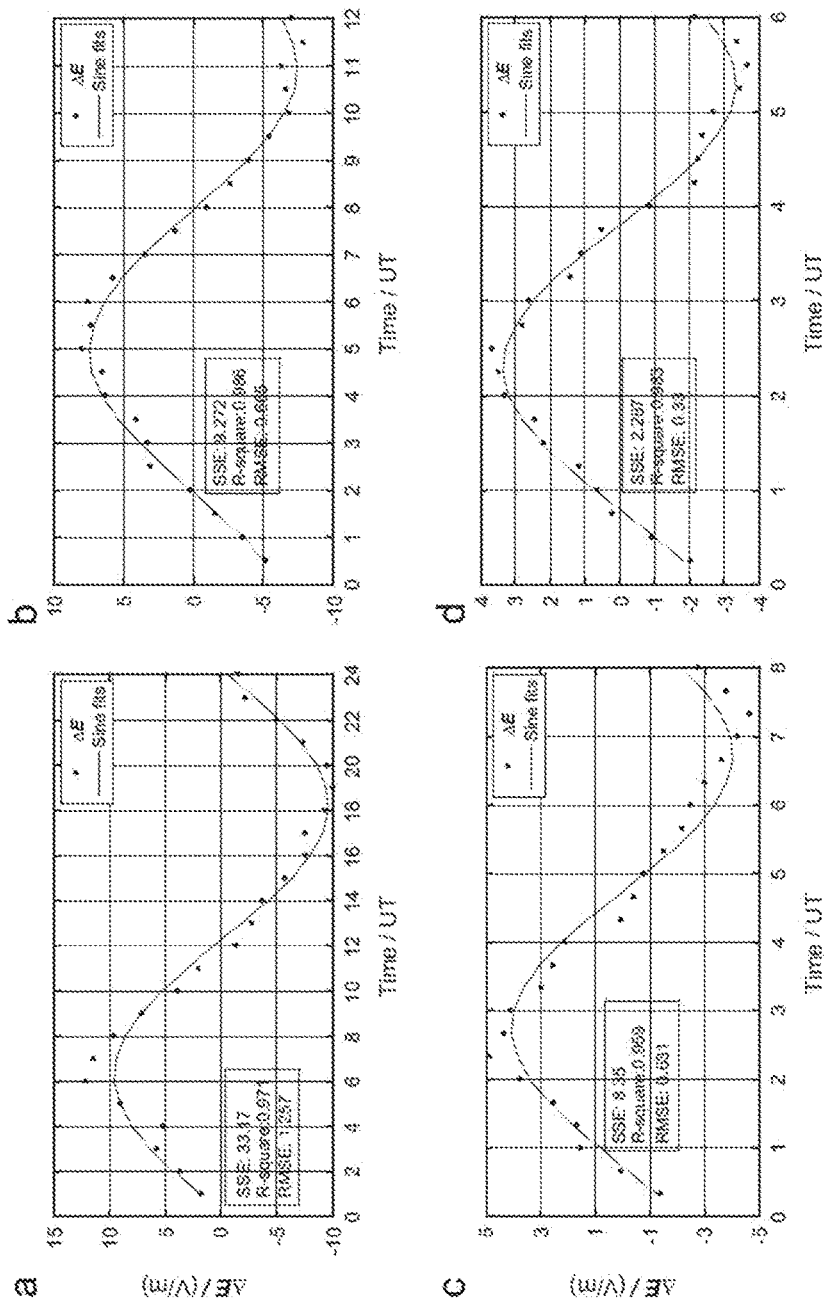
FIG. 14: Solar diurnal variation harmonics, namely 4 harmonic component and fitting curves for fair weather conditions in YBJ, Tibet ((B. Xu et al., Journal of Atmospheric and Solar-Terrestrial Physics 97 (2013) 85-90).
Figure 15:
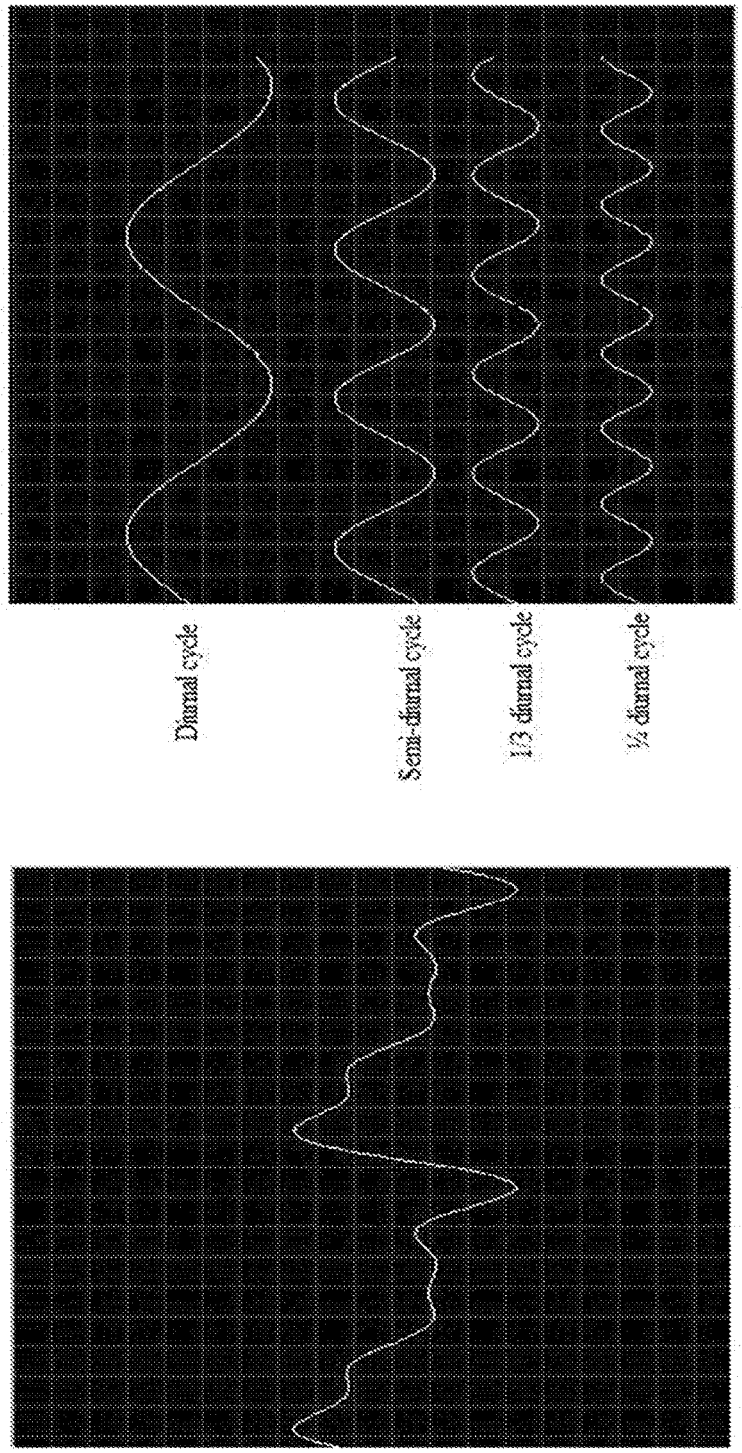
FIG. 15: It is a simulation figure from computer of daily variation of atmospheric electric field in fair weather conditions about YBJ, Tibet according some parameters from the article "Periodic variations of atmospheric electric field on fair weather" (B. Xu et al., Journal of Atmospheric and Solar-Terrestrial Physics 97 (2013) 85-90). The left side is the result of the combination of four harmonic component fitting curves. The right side are fitting curves of diurnal cycle, sSemi-diurnal cycle, ⅓ diurnal cycle and ¼ diurnal cycle. Start from UT 0:00 in the X-axis, and the strength of electricity is showed on the Y-axis. When applying the figure to different locations, we need to convert the UT (universe time) to local time.
Figure 16A:
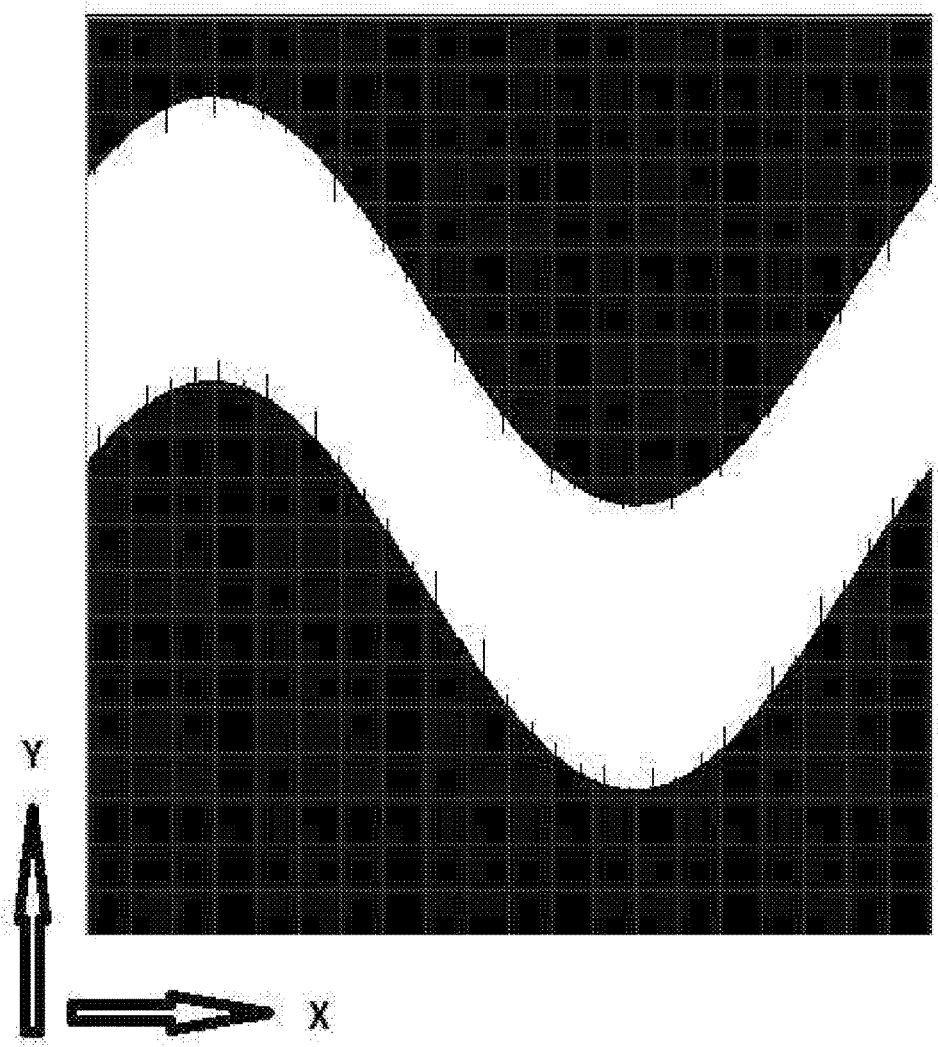
FIG. 16: (a) is a simulation figure from computer of yearly variation of atmospheric electric field in fair weather conditions about YBJ, Tibet according some parameters from the article as above. It looks like a ribbon with amplitude of the ribbon of 24.8V, with a wave low at the spring equinox and a high at the fall equinox. In (b) four harmonic component fitting curves when superimposed look like straight ribbons without waves. If we want to know how they look like in the real time, we can zoom into a very short moment, e,g, over 2 days, and they are looked like FIG. 15.
Figure 16:
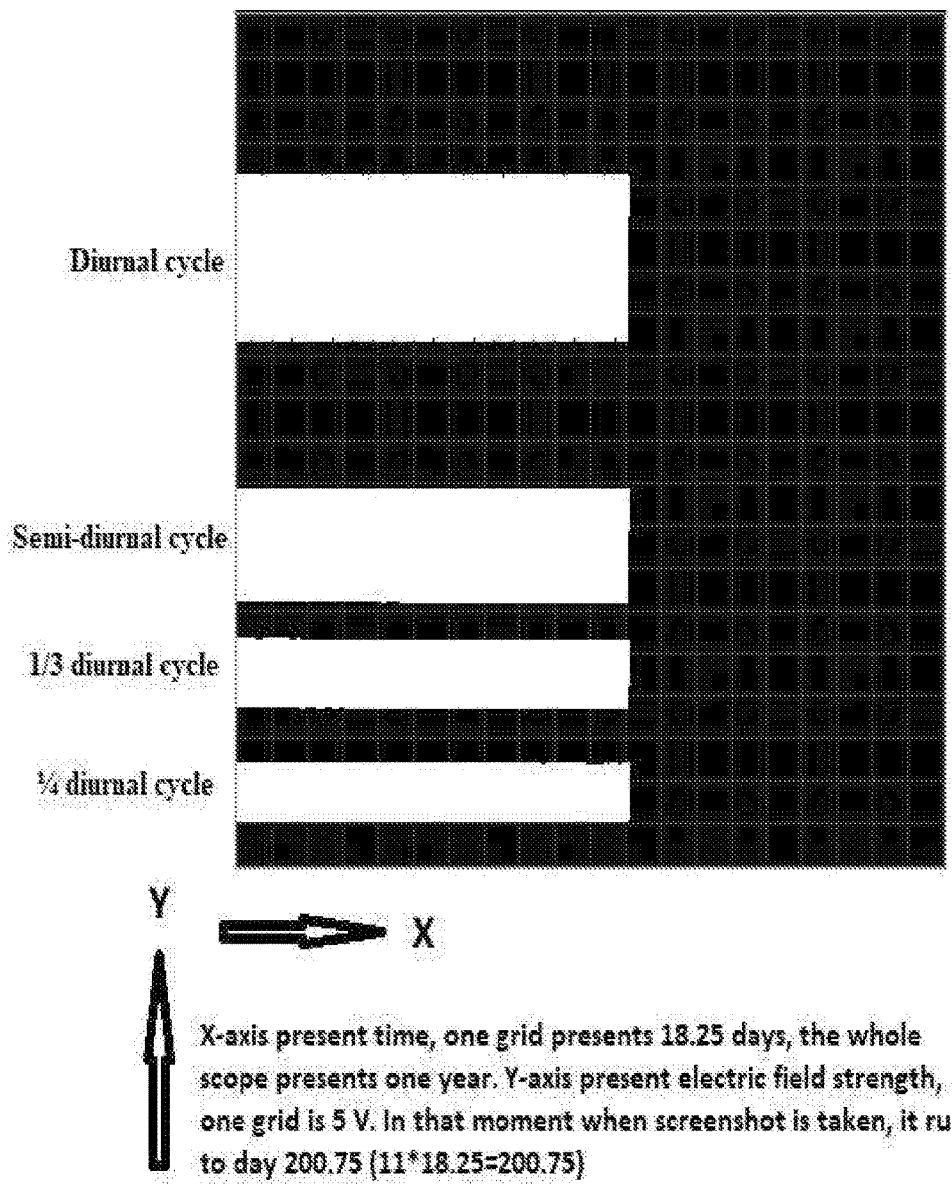

In one embodiment, as shown in FIG. 13, a bubble environment is constructed, such as a hollow ball (20) where the positive electrode (5) contacts the wall materials forming the bubble which is made of conductive material (8). The subject (12) and anything the subject is touching (e.g. sitting on a chair) is insulated from the wall of the bubble. The negative electrode (6) contacts the belly-button in the abdominal region of the subject. The conductive material used to construct the bubble enclosure must be permeable to the air for the subject to breathe with ease.

In a related embodiment the space boundaries are the side walls of an enclosure, in which case the electrodes are positioned proximal to the back and abdomen of the subject. In another related embodiment the space boundaries are the floor (base) and ceiling (top) of the enclosure, in which case the electrodes are positioned proximal to the head and feet of the subject. The conductive materials could be in the form of fibres, paint or metals. In another embodiment the electrodes do not need to contact a conductive material in order for an electric field to be generated in a space.

In one embodiment, the electrodes are positioned such that the positive electrode is in proximity to, or contacting a positive portion of body, and the negative electrode is in proximity to, or contacting a negative portion of the body (relative to the positive portion selected).

In one embodiment, when the electrodes are not contacting a subject, but are instead positioned on an article of furniture or clothing, the positive electrode is connected to conductive/semi-conductive material proximal to the head and the negative electrode is connected to conductive/semi-conductive material proximal to the feet of the subject.

In another embodiment, when the electrodes are contacting a subject, the positive electrode contacts the back of the subject and the negative electrode contacts the abdomen. In cases where the electrodes are contacting the subject, an anti-shock barrier such as a woven cloth can be wrapped around the surface of the electrode contacting the subject.

When a subject is in an environment where a wellness promoting electric field is being simulated according the systems and methods of the present disclosure, the subject may be resting, active, or receiving a treatment or therapy.

In one embodiment, the subject receives an acupuncture treatment in the environment where the desired electric field is generated (simulated). In another embodiment, the subject receives a massage treatment in the environment where the desired electric field is generated (simulated). In related embodiments the individual delivering the treatment or therapy is also in or in the vicinity of the environment where the desired electric field is generated (simulated).

In a further embodiment, the subject practices TaiChi or Qigong in the environment or in the vicinity of the environment where the desired electric field is generated (simulated).

The ease by which the present system and methods of the disclosure can be applied allow for the application of the present invention to help improve the wellbeing and health of a subject, including improving longevity, better quality of life, better work and productivity performance.

To support the healing process, the invention can be applied to ameliorate a number of disease conditions, such as:

Stroke, Sinus Infection, Sciatica, rheumatoid arthritis, Low Back Pain(Lumbago), Retention of Urine, renal colic, primary hypotension, primary dysmenorrheal, Premenstrual Syndrome, postoperative pain, periarthritis of the shoulder, peptic ulcer, neck pain, nausea and vomiting, morning sickness, Menopausal Syndrome, Male Energy Regeneration, longevity, leucopenia, knee pain, Jaundice, Irregular Periods, insomnia, Infertility, including hay fever, Impotence, Hypochondria Pain, Hemorrhoids, Migraine, Gastro-Intestinal Disorders, Facial Paralysis, facial pain, essential hypertension, Erectile dysfunction, Dysmenorrhea, Endometriosis, Edema, Diarrhea, Diabetes, Depression, dental pain, Cold and Flu, Chronic Pelvic Pain, Constipation, Carpal tunnel, Asthma, arthritis, Anti-Aging, allergic rhinitis, adverse reactions to radiation or chemotherapy, acute epigastralgia, acute and chronic gastritis, acid reflux, toothache, tinnitus, tennis elbow.

Using the system and methods of the present disclosure a subject who had felt distention in the right side of the middle abdomen for more than 10 years, was diagnosed as having liver cancer and was waiting for a transplant. After using the system and method of the present disclosure for two weeks, the subject's abdominal distention was reduced to 30% of what it was before using the system and methods. Following continued use for a three month period, the subject's cancer index was lowered significantly.

Another subject, had constipation for more than 7 years, defecating only every 3~4 days. After using the system and methods of the present disclosure for three days, the subject's intestines moved much better, allowing her to defecate every morning.

A third subject was very thin and had a poor appetite. After one month of using the system and method of the present disclosure, the subject's appetite had improved and the subject had gained 5 Kg.

To gain a better understanding of the invention described herein, the following examples are set forth. It will be understood that these examples are intended to describe illustrative embodiments of the invention and are not intended to limit the scope of the invention in any way.

EXAMPLES

Figure 4:
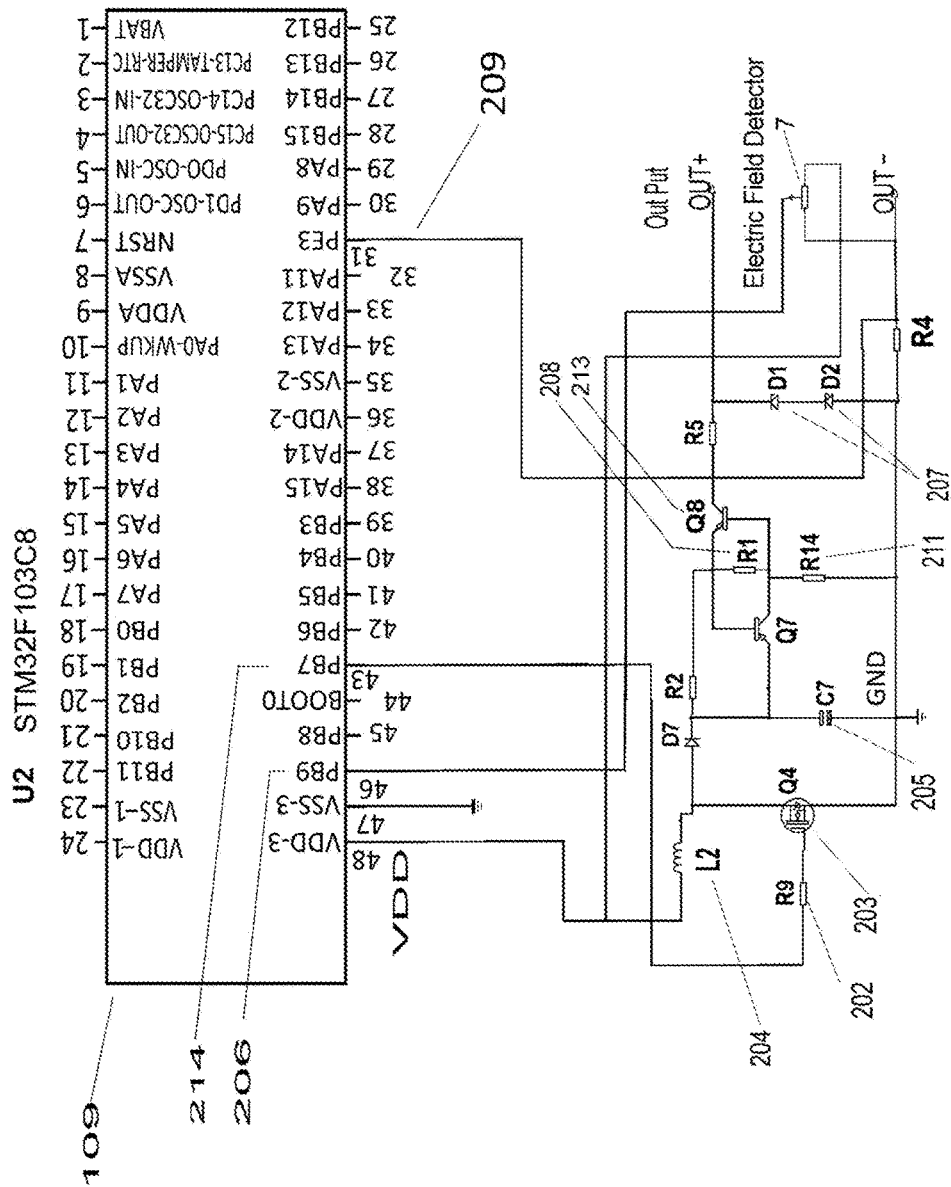
FIG. 4: An electrical schematic embodiment of the microprocessor based control sub-system according to present disclosure.

Example 1: Exemplary System for Generating a Smooth and Incrementally Changing Electric Field in Real-Time FIGS. 1, 4 and 5 provide an exemplary system for creating a positive smooth and incrementally changing electric field in a space, which simulates a well-being promoting electric field. All of the components used to construct the system are readily available in the marketplace to one skilled in the art.

Figure 20:
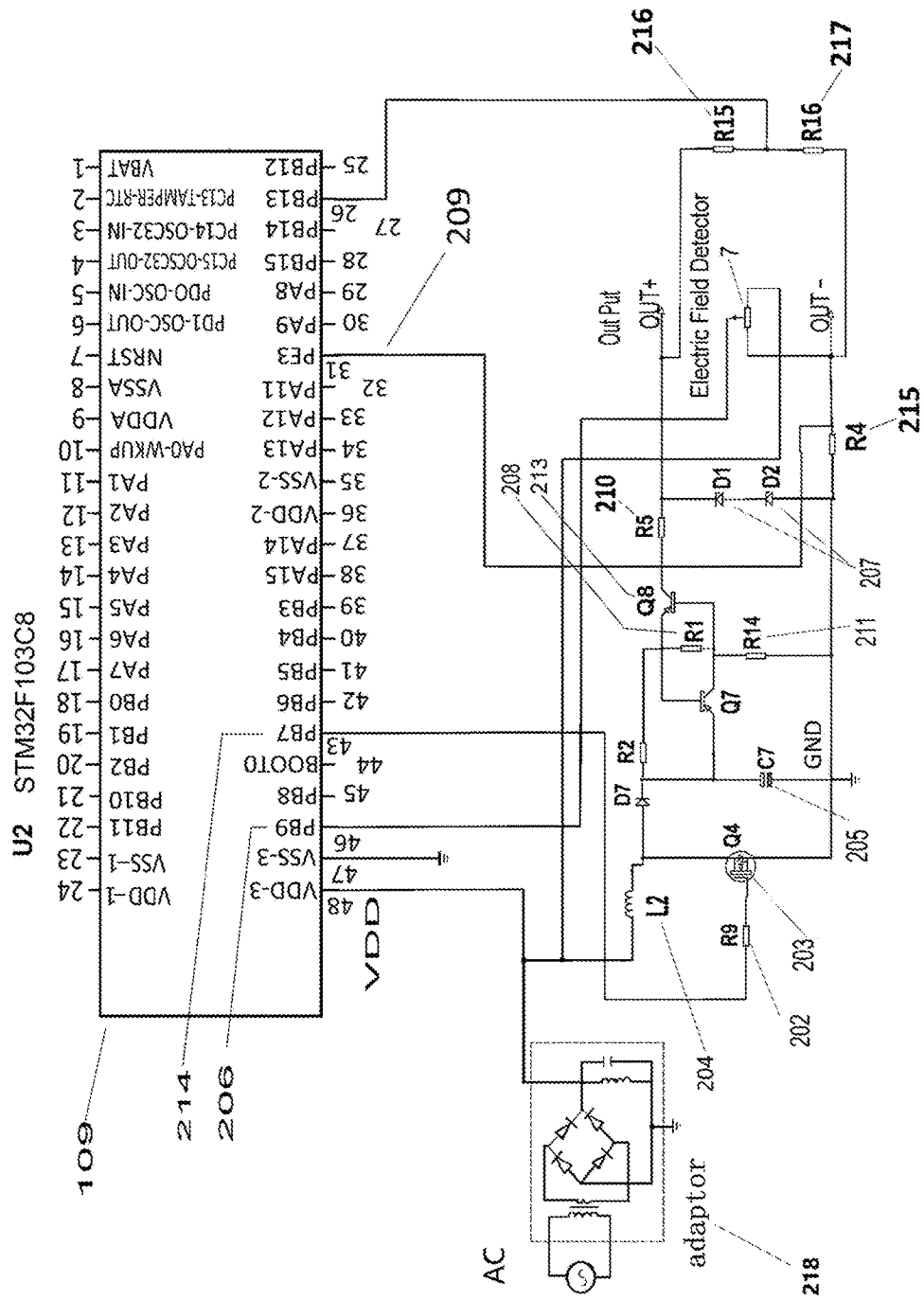
FIG. 20: A new electrical schematic embodiment of the microprocessor based control sub-system according to present disclosure, based on FIG. 4, adding an AC power source and providing for its conversion to a DC input, and voltage detecting resistors R15 and R16.

With reference to FIGS. 4 and 20, a microcontroller U2 stores a set of strength values for a desired electric field profile related with date and time, or formulas to calculate strength of electric field based on the date and time. A real time clock (see date and time input of FIG. 1) is operatively associated with the microcontroller. When the microcontroller reads (samples) the date and time, it determines the strength value(s) for the electric field to be generated by the system, and directs the function (output) of the PWM (Pulse Width Modulation) to the pin of PB7 (214) U2 of FIGS. 4 and 20. The PWM output is sent to R9 (202), which controls the on or off function of the switch Q4 (203). This results in the control of L2 (204) and C7 (205) to be charged to reach a target voltage. C7 has a big value of at least 45 UF, so that it can filter out pulses from the environment and from the PWM to reach a no pulse, smooth output, to make sure $dE/dt<0.01$ v when dt less than 1 second.

The power source can be any kind of source: AC, photovoltaic and DC. As exemplified in FIG. 20, the power source is AC, and the AC is converted to a DC by an adaptor (218).

This system has various feedback loops. The microcontroller is operatively associated with an ADC (analog digital converter) to read the real strength of electric field in the target environment, Pin PB9 (206) of FIGS. 4 and 20, and compares the real strength of electric field and the target strength of desired electric field profile. When the effective electric field reaches the desired value, the microcontroller will stop the output of PWM. Otherwise, it will continue to output a PWM signal. The process steps implemented by the microcontroller on the basis of software or other instructions governing the control functions of the microcontroller are shown in FIG. 5.

Other feedback loops are embodied in the current and voltage overage protection modules or subsystems (e.g. see FIGS. 19 and 20). A first feedback loop for current protection is represented by R1 (208), R2 (210), R14 (211), Q7 (212) and Q8 (213) in FIGS. 4 and 20. The strength of the electric field output will drop down immediately when the current of the circuit reaches a certain value, for example, 5 MA or some other pre-set amount.

A second current overage feedback loop is represented by R4 (215), and PE3 (209) and the microcontroller U2 shown in FIGS. 4 and 20.

A voltage overage feedback loop is represented by Zener diodes D1 and D2 (207). When the voltage is over a certain pre-set amount, D1 and D2 will be open and bring down the voltage running through the system.

FIGS. 1 and 19 are block diagrams of systems according to the present disclosure to create a positive, smooth, incrementally changing (variable) electric field. It consists of the following modules: microcomputer unit (109), PWM unit (103), (low) DC input (101), switch (102), converter & filter (104), DC output (105), two inputs and two outputs and two feedbacks circuits. Inputs are the DC input (101) which can be from a direct DC power source or from a converted power input from an alternative power source, and the date & time input.

Outputs are the positive electrode (5) output and negative electrode (6) output which can be configured in a target environment as shown in FIGS. 2, 3, 11 and 13. The two feedback circuits are the effective electric field sampling (110) provided by the electric field detector (7) (otherwise known as an electric field meter) and overcurrent feedback loop (111) as shown in FIGS. 1-4 and 11-13.

The PWM, DC input (which receives direct or converted DC power from a power source, e.g. a battery), switch, and DC output are features of DC to DC convert circuit (subsystem). PWM technology is commonly used in DC to DC conversion or switched mode power supply. PWM is applied to convert a normal low voltage DC to a non-permanent (variable) DC output.

The control circuitry (subsystem) is based on the microcomputer (microcontroller/microprocessor) unit accepting inputs, including the date and time input. The date and time are correlated to a set of stored or calculable electric field strengths in order to generate or not generate a signal to activate the PWM module/unit and thereby control pulse width emitted. The width of the pulse in turn regulates the switch to turn it on or off. As the switch is turned on or off, the DC input from the power source regulates the charge and discharge of the converter and filter module/unit. The converter can be an inducer or transformer that converts a DC voltage to a higher voltage, while the filter can be any electronic filter such as a capacitor. The result is the a slow fluctuating, no pulse signal ready for output via the electrode pairing to generate the desired variable electric field.

The feedback loops monitor the parameters which determine how the microcomputer will change or modulate the signal sent to the PWM unit to alter the width of pulse which thereby controls the ultimate DC output at any given point in time, rendering the system output stable and controllable, on a generally incremental and fine level for optimal simulation of a wellness promoting electric field.

In FIG. 5, exemplary microcontroller mediated method steps for the control of the electric field output are set out. The microcontroller has a real time clock, and accepts other inputs from users to set, among other things, the clock's date and time (301). From time to time, the microcontroller reads the real date and time from the clock (302), and conducts the processing operation of comparing the strength of effective electric field sampled by the electric field detector (304) with the target strength of desired electric field profile (303). Once the target strength of the electric field Ut, is compared to the effective (real time) strength of electric field, Ur (305), if Ut>Ur, the microcontroller sends a signal to stop the pulse from PWM module (306), or otherwise prorates/adjusts the signal (307) to achieve a DC output in line with the target output required to achieve a wellness promoting electric field strength in the target environment. This cycle of sampling followed by PWM signal modulation is repeated with the frequency required to achieve a wellness promoting electric field cycle.

The disclosures of all patents, patent applications, publications and database entries referenced in this specification are hereby specifically incorporated by reference in their entirety to the same extent as if each such individual patent, patent application, publication and database entry were specifically and individually indicated to be incorporated by reference.

Although the invention has been described with reference to certain specific embodiments, various modifications thereof will be apparent to those skilled in the art without departing from the spirit and scope of the invention. All such modifications as would be apparent to one skilled in the art are intended to be included within the scope of the following claims.

The embodiments of the invention in which an exclusive property or privilege is claimed are defined as follows:

1. A method comprising the steps of:
   a) providing a power source and generating a DC input to a converter to produce a DC output and generate a DC electric field in a space between a positive electrode and a negative electrode where a subject is located, wherein the positive electrode is positioned proximal to the head or torso of the subject and the negative electrode is positioned proximal to the feet or abdomen of the subject;
   b) detecting an actual electric field in the space between the positive electrode and negative electrode using a first detector and transmitting information about the actual electric field from the first detector to a microprocessor;
   c) processing the information regarding the actual electric field using the microprocessor, the microprocessor being configured to receive and process the information to direct the generation of the DC electric field in real-time such that it simulates a fair weather electric field;
   d) modulating the strength of the DC electric field using a pulse width modulator operatively associated with a switch to regulate the DC output, wherein said pulse width modulator and switch are controlled by the microprocessor, which directs the operation of the pulse width modulator and switch to generate the DC electric field that simulates the fair weather electric field;
   e) further modulating the DC output by detecting an over-voltage of a voltage as the converter produces the DC output using a second detector and transmitting information regarding the over-voltage to the microprocessor to facilitate the adjustment of the DC output by one or more of the steps of changing a pulse width of a pulse width modulator, storing the over-voltage in a capacitor, and adjusting the voltage when it is over a certain pre-set amount; and
   f) connecting the capacitor to the DC output to filter out any pulse from an environment outside of the space between the positive and negative electrodes or from a circuit consisting of the converter, first detector, second detector, the microprocessor, and the pulse width modulator to ensure the DC output is DC; and
   wherein the strength of the simulated fair weather electric field is calculated as an inland rhythm: $E=A*\{162.8+(24.8*COS(day\ in\ the\ year-266)*2Pi/365)+9.7*COS((second\ in\ the\ day\ by\ hour\ format-6.5)*2Pi/24)+6.6*COS((second\ in\ the\ day\ by\ hour\ format-5)*2Pi/12)+4*COS((second\ in\ the\ day\ by\ hour\ format-3)*2Pi/8)+3.3*COS((second\ in\ the\ day\ by\ hour\ format-2.3)*2Pi/6\}$, where A is ration factor between 1 to 5 or wherein the strength of the simulated fair weather field is calculated as an ocean rhythm: $E=B*\{132.2+20.4\ Sin(t/24*360-191.2)+6.1\ Sin(2t/24*360-239.2)+2.2\ Sin(3t/24*360-193.7)+1.6\ Sin(4t/24*360-344.1)\}$, where B is a ration factor between 1 to 5 and t is time in the day by hour format.

2. The method according to claim 1, wherein the subject is a human subject.

3. The method according to claim 2, wherein the human subject is practicing Tai Chi or Qigong in the space between the positive electrode and negative electrode.

4. The method according to claim 3, wherein the human subject is receiving a therapy in the space between the positive electrode and negative electrode.

5. The method according to claim 1, wherein the positive electrode and negative electrode are each positioned on an article of furniture.

6. The method according to claim 5, wherein the article of furniture is a chair, stool, bench, sofa, bed, desk, or table.

7. The method according to claim 1, wherein the microprocessor directs the generation of the DC electric field to simulate the fair weather electric field cycle by performing a series of repeating steps comprising:
   i. Storage a table of field strengths (Ut) correspond to date and time or a formula in the microprocessor;
   ii. determining an actual date and time;
   iii. search the table or use the formula to get the electric field strength (Ut);
   iv. comparing the strength of the actual electric field (Ur) detected by the first detector with the fair weather field strength (Ut) selected to promote the wellness of the subject at a date and time corresponding to the actual date and time; and
   v. sending a signal to the pulse width modulator to regulate the DC output.

8. The system according to claim 7, wherein the microprocessor directs the generation of the DC electric field to simulate the electric field cycle by repeatedly performing a series of steps comprising:
   i Storage a table of field strengths (Ut) correspond to date and time or a formula in microprocessor;
   ii determining an actual date and time;
   iii search the table or use the formula to get the electric field strength (Ut);
   iv comparing the strength of the actual electric field (Ur) detected by the first detector with the fair weather field strength (Ut) selected to promote the wellness of the subject at a date and time corresponding to the actual date and time; and
   v sending a signal to the pulse width modulator to regulate the DC output.

9. The method according to claim 1, wherein at any given point in time, the change in the strength of the simulated fair weather electric field divided by time (dE/dT) is less than 0.01 v when dT less than 1 second.

10. The method according to claim 1 wherein the capacitor is at least 270 UF.

11. A method according to claim 1, further comprising the steps of detecting an over-current as the converter produces the DC output using a third detector and transmitting information regarding the over-current to the microprocessor to facilitate the adjustment of the DC output.

12. The method according to claim 1, wherein the enclosed space is a room, booth, cabin, or bubble enclosure.

13. The method according to claim 1, wherein the positive electrode and negative electrode are each positioned on a surface of a wall, floor, or ceiling of the enclosed space.

14. The method according to claim 1, wherein the positive electrode and negative electrode are each positioned on an article of clothing on the subject.

15. The method according to claim 1, wherein the DC electric field simulates a Carnegie curve, solar diurnal, annual, monthly, seasonal, fifteen minute, 10 year, 12 year, 60 year, or 180 year electric field cycle.

16. A system configured to perform the method according to claim 1.

* * * * *